United States Patent
Simanzhenkov et al.

(10) Patent No.: US 9,993,798 B2
(45) Date of Patent: Jun. 12, 2018

(54) COMPLEX COMPRISING OXIDATIVE DEHYDROGENATION UNIT

(71) Applicant: NOVA Chemicals (International) S.A., Fribourg (CH)

(72) Inventors: Vasily Simanzhenkov, Calgary (CA); Leonid Modestovich Kustov, Moscow (RU); Aleksey Victorovich Kucherov, Moscow (RU); Elena Dmitrievna Finashina, Moscow (RU); Xiaoliang Gao, Calgary (CA); Edward Christopher Foy, Calgary (CA); Claire Jeannine Ennis, Calgary (CA)

(73) Assignee: NOVA Chemicals (International) S.A., Fribourg (CH)

(*) Notice: Subject to any disclaimer, the term of this patent is extended or adjusted under 35 U.S.C. 154(b) by 15 days.

(21) Appl. No.: 15/366,277

(22) Filed: Dec. 1, 2016

(65) Prior Publication Data
US 2017/0106346 A1    Apr. 20, 2017

Related U.S. Application Data

(63) Continuation of application No. 13/783,727, filed on Mar. 4, 2013, now Pat. No. 9,545,610.

(51) Int. Cl.
*B01J 19/00*    (2006.01)
*B01J 19/24*    (2006.01)
(Continued)

(52) U.S. Cl.
CPC ......... *B01J 19/2475* (2013.01); *B01J 19/242* (2013.01); *B01J 19/245* (2013.01);
(Continued)

(58) Field of Classification Search
CPC ........ B01J 19/00; B01J 19/0046; B01J 19/24; B01J 19/2415; B01J 19/242; B01J 19/245;
(Continued)

(56) References Cited

U.S. PATENT DOCUMENTS 3,420,911 A    1/1969    Woskow et al.
3,420,912 A    1/1969    Woskow et al.
(Continued)

FOREIGN PATENT DOCUMENTS

DE    19620542 A1    11/1997
EP    0 407 091 A1    9/1991
(Continued)

OTHER PUBLICATIONS

Al-Baghli, Nadhir A. and Loughlin, Kevin F.; Binary and Ternary Adsorption of Methane, Ethane, and Ethylene on Titanosilicate ETS-a0 Zeolite; J. Chem. Eng. Data 2006, 51, pp. 248-254.
(Continued)

*Primary Examiner* — Natasha E Young
(74) *Attorney, Agent, or Firm* — Lawrence T. Kale

(57) ABSTRACT

Oxidative dehydrogenation of paraffins to olefins provides a lower energy route to produce olefins. Oxidative dehydrogenation processes may be integrated with a number of processes in a chemical plant such as polymerization processes, manufacture of glycols, and carboxylic acids and esters. Additionally, oxidative dehydrogenation processes can be integrated with the back end separation process of a conventional steam cracker to increase capacity at reduced cost.

14 Claims, 12 Drawing Sheets

(51) Int. Cl.

| | | |
|---|---|---|
| *C08F 110/02* | (2006.01) | |
| *C07C 5/48* | (2006.01) | |
| *C07C 7/167* | (2006.01) | |
| *C07C 51/16* | (2006.01) | |
| *C07C 67/04* | (2006.01) | |
| *C07B 39/00* | (2006.01) | |
| *B01J 23/28* | (2006.01) | |
| *B01J 23/755* | (2006.01) | |
| *B01J 23/847* | (2006.01) | |
| *B01J 27/02* | (2006.01) | |
| *B01J 27/057* | (2006.01) | |
| *B01J 35/02* | (2006.01) | |
| *B01J 35/06* | (2006.01) | |
| *B01J 35/10* | (2006.01) | |
| *C07C 11/04* | (2006.01) | |
| *C10G 5/04* | (2006.01) | |
| *C10G 9/36* | (2006.01) | |
| *C10G 70/02* | (2006.01) | |
| *C10G 70/04* | (2006.01) | |
| *C10G 70/06* | (2006.01) | |

(52) U.S. Cl.
CPC .............. *C07B 39/00* (2013.01); *C07C 5/48* (2013.01); *C07C 7/167* (2013.01); *C07C 51/16* (2013.01); *C07C 67/04* (2013.01); *C08F 110/02* (2013.01); *B01J 2219/24* (2013.01)

(58) Field of Classification Search
CPC ...... B01J 19/2475; B01J 23/00; B01J 23/002; B01J 23/16; B01J 23/24; B01J 23/28; B01J 23/70; B01J 23/72; B01J 23/755; B01J 23/76; B01J 23/84; B01J 23/847; B01J 27/00; B01J 27/02; B01J 27/057; B01J 27/0576; B01J 35/00; B01J 35/02; B01J 35/06; B01J 35/065; B01J 35/10–35/1014; B01J 2219/00; B01J 2219/24; C07C 5/00; C07C 5/42; C07C 5/48; C07C 7/00; C07C 7/148; C07C 7/163; C07C 7/167; C07C 11/00–11/04; C07C 51/00; C07C 51/16; C07C 67/00; C07C 67/04; C10G 5/00; C10G 5/04; C10G 9/00; C10G 9/34; C10G 9/36; C10G 70/00; C10G 70/02; C10G 70/04–70/06; C10G 2400/00; C10G 2400/20; C08F 110/00; C08F 110/02
See application file for complete search history.

(56) References Cited

U.S. PATENT DOCUMENTS

| | | |
|---|---|---|
| 3,904,703 A | 9/1975 | Lo et al. |
| 4,250,346 A | 2/1981 | Young et al. |
| 4,450,313 A | 5/1984 | Eastman et al. |
| 4,524,236 A | 6/1985 | McCain |
| 4,596,787 A | 6/1986 | Manyik et al. |
| 4,845,253 A | 7/1989 | Bowman |
| 4,899,003 A | 2/1990 | Manyik et al. |
| 4,917,711 A | 4/1990 | Xie et al. |
| 5,011,591 A | 4/1991 | Kuznicki |
| 5,202,517 A | 4/1993 | Minet et al. |
| 5,744,687 A | 4/1998 | Ramachandran et al. |
| 5,859,304 A | 1/1999 | Barchas et al. |
| 6,423,881 B1 | 7/2002 | Yang et al. |
| 6,517,611 B1 | 2/2003 | Kuznicki et al. |
| 6,518,476 B1 | 2/2003 | Culp et al. |
| 6,521,808 B1 | 2/2003 | Ozkan et al. |
| 6,566,573 B1 | 5/2003 | Bharadwaj et al. |
| 6,581,476 B1 | 6/2003 | Fremercy |
| 6,624,116 B1 | 9/2003 | Bharadwaj et al. |
| 6,747,066 B2 | 6/2004 | Wang et al. |
| 6,818,189 B1 | 11/2004 | Adds et al. |
| 6,867,166 B2 | 3/2005 | Yang et al. |
| 6,891,075 B2 | 5/2005 | Liu |
| 6,992,112 B2 | 1/2006 | Wang et al. |
| 7,211,688 B2 | 5/2007 | Clarke et al. |
| 7,319,179 B2 | 1/2008 | Lopez Nieto et al. |
| 7,411,107 B2 | 8/2008 | Lucy |
| 8,017,825 B2 | 9/2011 | Kuznicki et al. |
| 2010/0256432 A1 | 10/2010 | Arnold et al. |
| 2011/0245571 A1 | 10/2011 | Kustov et al. |

FOREIGN PATENT DOCUMENTS

| | | |
|---|---|---|
| GB | 12 13 181 | 11/1970 |
| JP | 59172427 A | 9/1984 |
| JP | 59172428 A | 9/1984 |
| WO | 99/51339 A1 | 10/1999 |
| WO | 2005/058498 A1 | 6/2005 |
| WO | 2006/130288 A1 | 12/2006 |

OTHER PUBLICATIONS

Peri, J.B. and Hensley, Jr., A.L.; The Surface Structure of Silica Gel; The Journal of Physical Chemistry; vol. 72, No. 8, Aug. 1968; pp. 2926-2933.

COMPLEX COMPRISING OXIDATIVE DEHYDROGENATION UNIT

CROSS REFERENCE TO RELATED PATENT APPLICATION

This application is a continuation of U.S. application Ser. No. 13/783,727, now U.S. Pat. No. 9,545,610 filed on Mar. 4, 2013, entitled "Complex Comprising Oxidative Dehydrogenation Unit", which is herein incorporated by reference in its entirety.

FIELD OF THE INVENTION

The present invention relates to an improvement to chemical complexes having an ethane cracker and a $C_2$ splitter. There is a marked increase in the availability of ethane and natural gas liquids particularly in North America such as unconventional shale gas. There are a number of proposals to build chemical complexes to crack ethane and produce petrochemical products. In cracking ethane there are many high energy steps. Cracking furnaces are energy intensive, as is the downstream separation train as the low and close molecular weight compounds such as methane, ethane and ethylene need to be separated. Plant managers and engineer tend to be conservative and are unlikely to go to lower energy oxidative dehydrogenation processes as they have not been commercially implemented to any extent. Incremental expansion of a cracker or a cooling train is expensive. As plants expand, a method to increase capacity at a reduced cost is to install an oxidative dehydrogenation unit intermediate the cracker and the separation train or combining an oxidative dehydrogenation reactor with the separation train (e.g., the $C_2$ splitter). Recycled streams containing ethane and ethylene could pass through the oxidative dehydrogenation unit without requiring expansion of the cracker and potentially then pass to the separation stage without putting an undue load on the cooling train.

BACKGROUND OF THE INVENTION

There are a number of United States patents assigned to Petro-Tex Chemical Corporation issued in the late 1960's that disclose the use of various ferrites in a steam cracker to produce olefins from paraffins. The patents include U.S. Pat. Nos. 3,420,911 and 3,420,912 in the names of Woskow et al. The patents teach the use of ferrites such as zinc, cadmium, and manganese ferrites (i.e., mixed oxides with iron oxide) in oxidative dehydrogenation. The ferrites are introduced into a dehydrogenation zone at a temperature from about 250° C. up to about 750° C. at pressures less than 100 psi (689 kPa) for a time less than 2 seconds, typically, from 0.005 to 0.9 seconds. The reaction appears to take place in the presence of steam that may tend to shift the equilibrium in the "wrong" direction. Additionally, the reaction takes place in the presence of a catalyst not of the present invention.

In the Petro-Tex patents, the metal ferrite (e.g., $MFeO_4$ where, for example, M is Mg, Mn, Co, Ni, Zn or Cd) is circulated through the dehydrogenation zone and then to a regeneration zone where the ferrite is reoxidized and then fed back to the dehydrogenation zone.

The Great Britain Patent No. 1,213,181, which seems to correspond in part to the above Petro-Tex patents, discloses that nickel ferrite may be used in the oxidative dehydrogenation process. The reaction conditions are comparable to those of above noted Petro-Tex patents.

U.S. Pat. No. 6,891,075 issued May 10, 2005 to Liu, assigned to Symyx Technologies, Inc. teaches a catalyst for the oxidative dehydrogenation of a paraffin (alkane) such as ethane. The gaseous feedstock comprises at least the alkane and oxygen, but may also include diluents (such as, argon, nitrogen, etc.) or other components (such as, water or carbon dioxide). The dehydrogenation catalyst comprises at least about 2 weight % of NiO and a broad range of other elements, preferably, Nb, Ta, and Co. While NiO is present in the catalyst, it does not appear to be the source of the oxygen for the oxidative dehydrogenation of the alkane (ethane).

U.S. Pat. No. 6,521,808 issued Feb. 18, 2003 to Ozkan, et al, assigned to the Ohio State University teaches sol gel supported catalysts for the oxidative dehydrogenation of ethane to ethylene. The catalyst appears to be a mixed metal system, such as, Ni—Co—Mo, V—Nb—Mo possibly doped with small amounts of Li, Na, K, Rb, and Cs on a mixed silica oxide/titanium oxide support. The catalyst does not provide the oxygen for the oxidative dehydrogenation, rather, gaseous oxygen is included in the feed.

U.S. Pat. No. 4,450,313, issued May 22, 1984 to Eastman et al., assigned to Phillips Petroleum Company, discloses a catalyst of the composition $Li_2O—TiO_2$, which is characterized by a low ethane conversion not exceeding 10%, in spite of a rather high selectivity to ethylene (92%). The major drawback of this catalyst is the high temperature of the process of oxidative dehydrogenation, which is close to or higher than 650° C.

The preparation of a supported catalyst useful for low-temperature oxidative dehydrogenation of ethane to ethylene is disclosed in the U.S. Pat. No. 4,596,787 A issued Jun. 24, 1986 to Manyik et al., assigned to Union Carbide Corporation. A supported catalyst for the low-temperature gas-phase oxidative dehydrogenation of ethane to ethylene is prepared by (a) preparing a precursor solution having soluble and insoluble portions of metal compounds, (b) separating the soluble portion, (c) impregnating a catalyst support with the soluble portion and (d) activating the impregnated support to obtain the catalyst. The calcined catalyst has the composition

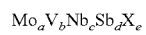

$$Mo_aV_bNb_cSb_dX_e$$

wherein X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9; b is 0.1-0.4; c is 0.001-0.2; d is 0.001-0.1; and e is 0.001-0.1 when X is an element. The patent fails to teach or suggest a co-commination of the catalyst and the support.

Other examples of the low temperature oxidative dehydrogenation of ethane to ethylene using a calcined oxide catalyst containing molybdenum, vanadium, niobium and antimony are described in U.S. Pat. No. 4,524,236 A, issued Jun. 18, 1985 and U.S. Pat. No. 4,250,346 A, issued Feb. 10, 1981, both assigned to Union Carbide Corporation. The calcined catalyst contains

$$Mo_aV_bNb_cSb_dX_e$$

in the form of oxides. The catalyst is prepared from a solution of soluble compounds and/or complexes and/or compounds of each of the metals. The dried catalyst is calcined by heating at 220 to 550° C. in air or oxygen. The catalyst precursor solutions may be supported onto an inorganic oxide (e.g., silica, aluminum oxide, silicon carbide, zirconia, titania or mixtures of these). The selectivity to ethylene may be greater than 65% for a 50% conversion of ethane.

The U.S. Pat. No. 6,624,116, issued Sep. 23, 2003 to Bharadwaj, et al. and U.S. Pat. No. 6,566,573 issued May 20, 2003 to Bharadwaj, et al., both assigned to Dow Global Technologies Inc., disclose Pt—Sn—Sb—Cu—Ag monolith systems that have been tested in an auto-thermal regime at T>750° C. where the starting gas mixture contains hydrogen ($H_2$: $O_2$=2:1, gas hourly space velocity (GHSV) of 180 000 $h^{-1}$). The catalyst composition is different from that of the present invention and the present invention does not contemplate the use of molecular hydrogen in the feed.

U.S. Pat. No. 4,524,236 issued Jun. 18, 1985 to McCain assigned to Union Carbide Corporation and U.S. Pat. No. 4,899,003, issued Feb. 6, 1990 to Manyik et al. assigned to Union Carbide Chemicals and Plastics Company Inc. disclose mixed metal oxide catalysts of V—Mo—Nb—Sb. At 375 to 400° C. the ethane conversion reached 70% with the selectivity close to 71 to 73%. However, this ethane conversion result was only achieved at very low gas hourly space velocities (i.e., 720 $h^{-1}$).

U.S. Pat. No. 7,319,179 issued Jan. 15, 2008 to Lopez-Nieto et al. assigned to Consejo Superior de Investigaciones Cientificas and Universidad Politecnica de Valencia discloses Mo—V—Te—Nb—O oxide catalysts that provided an ethane conversion of 50-70% and selectivity to ethylene up to 95% (at 38% conversion) at 360 to 400° C. The catalysts have the empirical formula $$MoTe_hV_iNb_jA_kO_x$$

where A is a fifth modifying element. The catalyst is a calcined mixed oxide (at least of Mo, Te, V and Nb), optionally supported on: (i) silica, alumina and/or titania, preferably silica at 20 to 70 wt % of the total supported catalyst or (ii) silicon carbide. The supported catalyst is prepared by conventional methods of precipitation from solutions, drying the precipitate and then calcining.

The preparation of a Mo—Te—V—Nb composition is described in WO 2005058498 A1, published 30 Jun. 2005 (corresponding to U.S. Published Application No. 2007149390 A1). Preparation of the catalyst involves preparing a slurry by combining an inert ceramic carrier with at least one solution comprising ionic species of Mo, V, Te, and Nb, drying the slurry to obtain a particulate product, pre-calcining the dried product at 150 to 350° C. in an oxygen-containing atmosphere and calcining the dried product at 350 to 750° C. under inert atmosphere. The catalyst prepared exhibits the activity and selectivity in the oxidation reaction comparable to the non-supported catalyst.

A process for manufacturing ethylene from gaseous feed comprising ethane and oxygen involving contacting the feed with a mixed oxide catalyst containing vanadium, molybdenum, tantalum and tellurium in a reactor to form an ethylene-containing effluent is disclosed in WO 2006130288 A1, published Dec. 7 2006, (also, published Sep. 2, 2010 as U.S. Published Application No. 20100222623, now abandoned) assigned to Celanese Int. Corp. The catalyst has a selectivity for ethylene of 50 to 80% thereby allowing oxidation of ethane to produce ethylene and acetic acid with high selectivity. The catalyst has the formula $$Mo_1V_{0.3}Ta_{0.1}Te_{0.3}O_z.$$

The catalyst is optionally supported on an inorganic oxide supported on a support selected from porous silicon dioxide, ignited silicon dioxide, kieselguhr, silica gel, porous and nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride, silicon carbide, and glass, carbon, carbon-fiber, activated carbon, metal-oxide or metal networks and corresponding monoliths, or is encapsulated in, preferably, silicon dioxide ($SiO_2$), phosphorus pentoxide ($P_2O_5$), magnesium oxide (MgO), chromium trioxide ($Cr_2O_3$), titanium oxide ($TiO_2$), zirconium oxide ($ZrO_2$) or alumina ($Al_2O_3$). The methods of preparation of the supported compositions involve the procedures of wet chemistry (solutions are impregnated into the solid support and then the materials are dried and calcined).

U.S. Pat. No. 5,202,517 issued Apr. 13, 1993 to Minet et al., assigned to Medalert Incorporated, teaches a ceramic tube for use in the conventional dehydrogenation of ethane to ethylene. The "tube" is a ceramic membrane in which the ethane flows inside the tube and hydrogen diffuses out of the tube to improve the reaction kinetics. The reactive ceramic is 5 micrometers thick on a 1.5 to 2 mm thick support.

U.S. Pat. No. 6,818,189 issued Nov. 16, 2004 to Adris et al., assigned to Saudi Basic Industries Corporation, teaches a process in which ceramic pellets are packed around a tubular reactor and different reactants flow around the outside and inside of the tube. The patent is directed to the oxidative dehydrogenation of ethane to ethylene.

There is a significant amount of art on the separation of ethylene and ethane using silver or copper ions in their +1 oxidation state. See U.S. Pat. No. 6,518,476 issued Feb. 11, 2003 to Culp et al. assigned to Union Carbide Chemicals & Plastics Technology Corporation at Col. 5, lines 10-15 and Col. 16, line 12 to Col. 17, line 57. NOVA Chemicals Corporation has also disclosed separation of olefins from non-olefins using ionic liquids (dithiolene in CA 2415064, now abandoned). Also see U.S. Pat. No. 6,120,692 issued Sep. 19, 2000 to Wang et al., assigned to Exxon Research and Engineering Company, the abstract of JP 59172428 published Sep. 29, 1984 and the abstract of JP 59172427 published Sep. 29, 1984.

U.S. Pat. No. 8,017,825 issued Sep. 13, 2011 to Kuznicki et al. assigned to the Governors of the University of Alberta contains a good outline of prior art for separation of ethane from ethylene and an adsorption method using modified ETS-10.

U.S. Pat. No. 7,411,107 issued Aug. 12, 2008 to Lucy et al., assigned to BP Chemicals Limited discloses a process for the separation of acetic acid from an oxidative dehydrogenation process to convert ethane to ethylene and acetic acid. The process uses a reversible complex of a metal salt (e.g., Cu or Ag) to separate ethylene (Col. 8). The patent then discloses the acetic acid may be separated from the liquids by a distillation (Col. 13, lines 35-40).

U.S. Published Application No. 20110245571 in the name of NOVA Chemicals (International) S.A. teaches oxidative dehydrogenation of ethane in a fluidized bed in contact with a bed of regenerative oxides to provide oxygen to the reactor. In this process, free oxygen is not directly mixed with the feedstock reducing the likelihood of decompositions.

U.S. Pat. No. 3,904,703 issued Sep. 9, 1975 to Lo et al., assigned to El Paso Products Company teaches a zoned or layered oxidative reactor in which following a zone for oxidative dehydrogenation there is an "oxidation zone" following a dehydrogenation zone to oxidize the hydrogen to water. Following the oxidation zone there is an adsorption bed to remove water from the reactants before they enter a subsequent dehydrogenation zone. This is to reduce the impact of water on downstream dehydrogenation catalysts.

U.S. Published Application No. 20100256432 published Oct. 7, 2010 in the name of Arnold et al., assigned to Lummus discloses in paragraphs 86-94 methods to remove residual oxygen from the product stream. A combustible such as hydrogen or a hydrocarbon may be added to the product stream to eliminate residual oxygen. The patent refers to a catalyst but does not disclose its composition. As noted above, it may then be necessary to treat the product stream to eliminate water.

U.S. Pat. No. 6,518,476 issued Feb. 11, 2003 to Culp et al., assigned to Union Carbide Chemicals & Plastics Technology Corporation discloses a process for coupling lower paraffins, such as, methane and then oxidative dehydrogenation of the coupled product to produce olefins such as ethylene and propylene.

None of the above art teaches or suggests a chemical complex in which intermediate a cracker and a separation train there is an oxidative dehydrogenation process.

The present invention seeks to provide a novel chemical complex in which there is an oxidative dehydrogenation process to dehydrogenate ethane to ethylene intermediate a chemicals cracker (e.g., a steam cracker) and the associated downstream separation units. This will provide expansion capacity at reduced operating costs. More particularly, in one aspect the overheads from the $C_2$ splitter could be passed through the oxidative dehydrogenation unit to reduce the ethane content (polish the product stream). In some cases, the upper portion of the rectifying portion of the $C_2$ splitter is used to reduce very low amounts of residual ethane in the ethylene. The technology of the present patent application may be applied to a new ethylene manufacturing site (greenfield development) or could be a retrofit to an existing facility to expand capacity at a minimum cost.

SUMMARY OF THE INVENTION

The present invention provides a (petro)chemical complex comprising a steam cracker comprising a $C_2$ splitter, the improvement comprising integrating into the complex intermediate the cracker and the $C_2$ splitter a reactor for oxidative dehydrogenation of ethane in mixed stream comprising ethane and ethylene.

In an embodiment of the invention, the oxidative dehydrogenation unit is integrated with the feed stream to the $C_2$ splitter.

In an embodiment of the invention, the oxidative dehydrogenation unit is integrated with the overhead stream from the $C_2$ splitter.

In an embodiment of the invention, the oxidative dehydrogenation unit is integrated with the bottom stream from the $C_2$ splitter.

In an embodiment of the invention, the oxidative dehydrogenation unit is integrated with the $C_2$ splitter taking a feed from a lower tray from the $C_2$ splitter and returning the product to a higher tray in the $C_2$ splitter.

In an embodiment of the invention, the oxidative dehydrogenation unit is integrated with the feed stream to a hydrogenation unit to remove acetylene.

In an embodiment of the invention, the chemical complex is further comprised of one or more unit operations selected from the group consisting of absorption separation of ethane from ethylene, adsorption separation of ethane from ethylene, a high pressure polyethylene plant, a gas phase polyethylene plant, a slurry phase polyethylene plant, a solution phase polyethylene plant, an acetic acid plant, a vinyl acetate plant, an ethylene glycol plant, an ethanol plant, an ethylene halide plant, an ethanol dehydrogenation plant, an acetic acid dehydrogenation plant.

In an embodiment, the oxidative dehydrogenation reactor uses a catalyst selected from the group consisting of:
i) catalysts of the formula:

$$Ni_xA_aB_bD_dO_e$$

wherein
x is a number from 0.1 to 0.9, preferably from 0.3 to 0.9, most preferably from 0.5 to 0.85, most preferably 0.6 to 0.8;
a is a number from 0.04 to 0.9;
b is a number from 0 to 0.5;
d is a number from 0 to 0.5;
e is a number to satisfy the valence state of the catalyst;
A is selected from the group consisting of Ti, Ta, V, Nb, Hf, W, Y, Zn, Zr, Si and Al or mixtures thereof;
B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof;
D is selected from the group consisting of Ca, K, Mg, Li, Na, Sr, Ba, Cs, and Rb and mixtures thereof; and
O is oxygen; and
ii) catalysts of the formula $$Mo_fX_gY_hO_i$$

wherein
X is selected from the group consisting of Ba, Ca, Cr, Mn, Nb, Ta, Ti, Te, V, W and mixtures thereof;
Y is selected from the group consisting of Bi, Ce, Co, Cu, Fe, K, Mg, V, Ni, P, Pb, Sb, Si, Sn, Ti, U, and mixtures thereof;
f=1;
g is 0 to 2;
h=0 to 2, with the proviso that the total value of h for Co, Ni, Fe and mixtures thereof is less than 0.5;
i is a number to satisfy the valence state of the catalyst; iii) catalysts of the formula $$V_xMo_yNb_zTe_mMe_nO_p$$

wherein Me is a metal selected from the group consisting of Ta, Ti, W, Hf, Zr, Sb and mixtures thereof; and
x is from 0.1 to 3;
y is from 0.5 to 1.5;
z is from 0.001 to 3;
m is from 0.001 to 5;
n is from 0 to 2
and p is a number to satisfy the valence state of the mixed oxide catalyst
iv) catalysts of the formula $$Mo_aV_bNb_cTe_eO_n$$

wherein a=1.0; b=0.05 to 1.0, c=0.001 to 1.0, e=0.001 to 0.5, and n is determined by the oxidation states of the other elements.
v) catalysts of the formula $$Mo_aV_bX_cY_dZ_eM_fO_n$$

wherein X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); b=0.05 to 1.0;

c=0.001 to 1.0; d=0.001 to 1.0; e=0.001 to 0.5; and f=0.001 to 0.3; and n is determined by the oxidation states of the other elements.

In an embodiment of the invention, in the above catalyst n is 0.

In an embodiment of the invention, the oxidative dehydrogenation of ethane to ethylene is conducted at a temperature from 250° C. to 600° C., preferably 300° C. to 550° C., and a pressure from 0.5 to 100 psi (3.4 to 689.5 kPa) and has a productivity of not less than 1000 g of olefin per kg of catalyst per hour.

In an embodiment of the invention, the oxidative dehydrogenation reaction has a selectivity of not less than 80% to produce the corresponding olefin.

In an embodiment of the invention, the oxidative dehydrogenation catalyst is supported on inert porous ceramic membrane selected from oxides of titanium, zirconia, aluminum, magnesium, yttria, lantana, silica and their mixed compositions to provide from 0.1 to 20 weight % of said catalyst and from 99.9 to 80 weight % of said porous membrane.

In an embodiment of the invention, the oxidative dehydrogenation reactor comprises an outer shell and one or more internal ceramic tubes defining a separate flow passage for ethane down the interior of said tubes and an annular passage between the external shell of the reactor and the ceramic tubes defining a flow path for an oxygen containing gas.

In an embodiment of the invention, the ceramic tube further comprises an internal steel mesh and an external steel mesh.

In an embodiment of the invention, the chemical complex further comprises an oil-based olefin paraffin absorption unit.

In an embodiment of the invention, the chemical complex further comprises an adsorption olefin paraffin separation unit.

In an embodiment of the invention, the adsorbent comprises one or more metals ions in the +1 oxidation state selected from the group consisting of silver and copper, although care must be exercised in the use of these compounds when separating streams containing acetylene due to the potential of forming explosive mixtures.

In an embodiment of the invention, the adsorbent is selected from the group consisting of synthetic or natural zeolites.

In an embodiment of the invention, the adsorbent is selected from the group consisting of ZSM-5, ETS-4, CTS-1, and ion-exchanged ETS-10.

In an embodiment of the invention, the adsorbent is a metal dithiolene selected from the group of complexes of the formulae:

$$M[S_2C_2(R^1R^2)]_2;\quad (I)$$

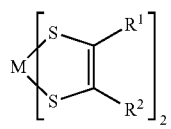

and $$M[S_2C_6(R^3R^4R^6R^7)]_2.\quad (ii)$$

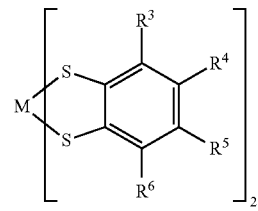

wherein M is selected from the group consisting of Fe, Co, Ni, Cu, Pd and Pt; and $R^1$, $R^2$, $R^3$, $R^4$, $R^5$, and $R^6$ are independently selected from the group consisting of a hydrogen atom, electron-withdrawing groups including those that are or contain heterocyclic, cyano, carboxylate, carboxylic ester, keto, nitro, and sulfonyl groups, hydrocarbyl radicals selected from the group consisting of $C_{1-4}$ alkyl groups, $C_{5-8}$ alkyl groups, $C_{2-8}$ alkenyl groups and $C_{6-8}$ aryl groups which hydrocarbyl radicals are unsubstituted or fully or partly substituted, preferably those substituted by halogen atoms.

In an embodiment of the invention, the ethylene halide plant reacts ethylene, optionally in the presence of oxygen, with a halide to produced one or more products selected from the group consisting of ethyl chloride, ethylene chloride, ethylene dichloride, ethyl bromide, ethylene bromide and ethylene dibromide.

In an embodiment of the invention, the acetic acid plant oxidizes/hydrates ethylene from the oxidative dehydrogenation process, the steam cracker or both to produce acetic acid.

In an embodiment of the invention, acetic acid from the acetic acid plant is reacted with ethylene to produce vinyl acetate.

In an embodiment of the invention, immediately downstream of the oxidative dehydrogenation reactor there is a low-temperature (typically below the temperature of the oxidative dehydrogenation reaction) reactor to consume residual oxygen without consuming more than 3 weight % of the ethylene produced.

In an embodiment of the invention, the fuel for said low-temperature reactor is selected from the group consisting of methane, hydrogen, carbon monoxide and mixtures thereof and is added to the product stream from the oxidative dehydrogenation reactor in an amount sufficient to consume residual oxygen.

In an embodiment of the invention, the said low-temperature reactor uses a catalyst which is a mixture of $Mn_2O_3$ and $CuMn_2O_4$ wherein said mixture has an empirical formula $Cu\text{---}Mn_xO_p$ wherein x is from 0.1 to 8 and p is a number to satisfy the valence state of the mixed catalyst.

DETAILED DESCRIPTION OF THE INVENTION

The Catalyst System

Figure 1:
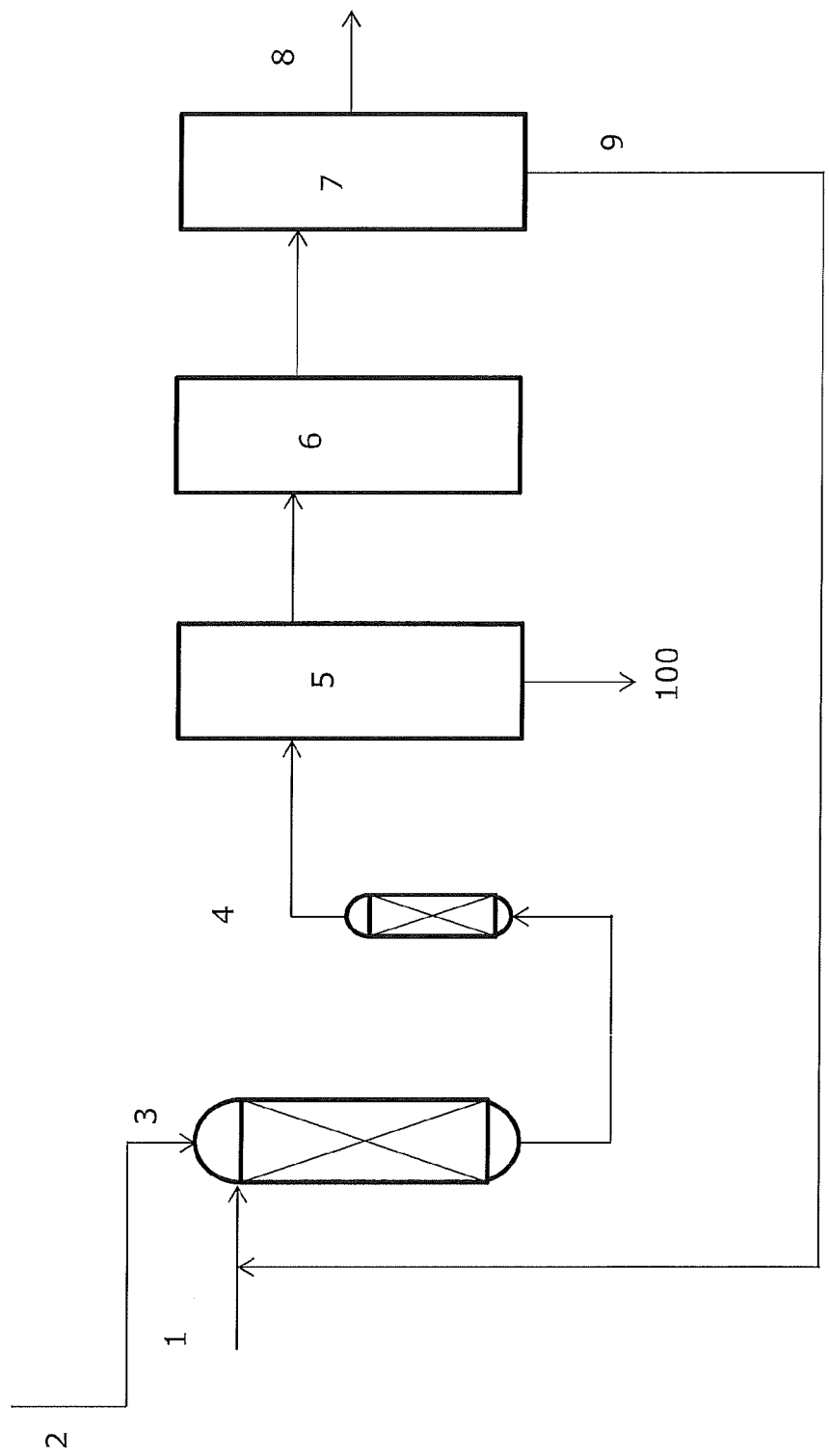
FIG. 1 is a schematic diagram of one embodiment of the present invention.

There are a number of catalysts which may be used in accordance with the present invention. The following catalyst systems may be used individually or in combination. One of ordinary skill in the art would understand that combinations should be tested at a laboratory scale to determine if there are any antagonistic effects when catalyst combinations are used.

The oxidative dehydrogenation catalyst of the present invention may be selected from the group consisting of:
i) catalysts of the formula:

$$Ni_xA_aB_bD_dO_e$$

wherein
x is a number from 0.1 to 0.9 preferably from 0.3 to 0.9, most preferably from 0.5 to 0.85, most preferably 0.6 to 0.8;
a is a number from 0.04 to 0.9;
b is a number from 0 to 0.5;
d is a number from 0 to 0.5;
e is a number to satisfy the valence state of the catalyst;
A is selected from the group consisting Ti, Ta, V, Nb, Hf, W, Y, Zn, Zr, Si and Al or mixtures thereof;
B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg and mixtures thereof;
D is selected from the group consisting of Ca, K, Mg, Li, Na, Sr, Ba, Cs, and Rb and mixtures thereof; and
O is oxygen; and
ii) catalysts of the formula:

$$Mo_fX_gY_hO_i$$

wherein
X is selected from the group consisting of Ba, Ca, Cr, Mn, Nb, Ta, Ti, Te, V, W and mixtures thereof;
Y is selected from the group consisting of Bi, Ce, Co, Cu, Fe, K, Mg V, Ni, P, Pb, Sb, Si, Sn, Ti, U and mixtures thereof;
f=1;
g is 0 to 2;
h is 0 to 2, with the proviso that the total value of h for Co, Ni, Fe and mixtures thereof is less than 0.5;
i is a number to satisfy the valence state of the catalyst; and
mixtures thereof.

In one embodiment, the catalyst is the catalyst of formula i) wherein x is from 0.5 to 0.85, a is from 0.15 to 0.5, b is from 0 to 0.1 and d is from 0 to 0.1. In catalyst i), typically A is selected from the group consisting of Ti, Ta, V, Nb, Hf, W, Zr, Si, Al and mixtures thereof, B is selected from the group consisting of La, Ce, Nd, Sb, Sn, Bi, Pb, Cr, Mn, Mo, Fe, Co, Cu, Ru, Rh, Pd, Pt, Ag, Cd, Os, Ir and mixtures thereof and D is selected from the group consisting of Ca, K, Mg, Li, Na, Ba, Cs, Rb and mixtures thereof.

In an alternative embodiment, the catalyst is catalyst ii). In some embodiments of this aspect of the invention, typically, X is selected from the group consisting of Ba, Ca, Cr, Mn, Nb, Ti, Te, V, W and mixtures thereof, Y is selected from the group consisting of Bi, Ce, Co, Cu, Fe, K, Mg, V, Ni, P, Pb, Sb, Sn, Ti and mixtures thereof.

One additional particularly useful family of catalysts iii) comprise one or more catalysts selected from the group consisting of a mixed oxide catalyst of the formula $$V_xMo_yNb_zTe_mMe_nO_p,$$

wherein Me is a metal selected from the group consisting of Ti, Ta, Sb, Hf, W, Y, Zn, Zr, La, Ce, Pr, Nd, Sm, Sn, Bi, Pb Cr, Mn, Fe, Co, Cu, Ru, Rh, Pd, Pt, Ag, Cd, Os, Ir, Au, and mixtures thereof; and
x is from 0.1 to 3, preferably from 0.5 to 2.0 most preferably from 0.75 to 1.5;
y is from 0.5 to 1.5, preferably from 0.75 to 1.0;
z is from 0.001 to 3, preferably from 0.1 to 2, most preferably from 0.5 to 1.5.
m is from 0.001 to 5, preferably from 1 to 4.
n is from 0 to 2, preferably n is 0, however when Me is present n is preferably from 0.5; to 1.5 and
p is a number to satisfy the valence state of the mixed oxide catalyst.

In a further embodiment, in the catalyst, the ratio of x:m is from 0.3 to 10, most preferably from 0.5 to 8, desirably from 0.5 to 6.

Another family of catalysts suitable for the oxidative dehydrogenation of ethane to ethylene includes catalysts of the formula $$Mo_aV_bNb_cTe_eO_n$$

wherein a=1.0; b=0.05 to 1.0, c=0.001 to 1.0, e=0.001 to 0.5, and n is determined by the oxidation states of the other elements.

Another family of catalysts suitable for the oxidative dehydrogenation of ethane to ethylene includes catalysts of the formula $$Mo_aV_bX_cY_dZ_eM_fO_n$$

wherein X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); b=0.05 to 1.0; c=0.001 to 1.0; d=0.001 to 1.0; e=0.001 to 0.5; and f=0.001 to 0.3; and n is determined by the oxidation states of the other elements.

The above catalysts may be used individually or in combinations. One of ordinary skill in the art would be aware to conduct routine tests to determine if there are antagonistic interactions between two or more catalyst which are being considered.

The methods of preparing the catalysts are known to those skilled in the art.

For example, the catalyst may be prepared by mixing aqueous solutions of soluble metal compounds such as hydroxides, sulphates, nitrates, halides, lower (C₁₋₅) mono or di carboxylic acids and ammonium salts or the metal acid per se. For instance, the catalyst could be prepared by blending solutions such as ammonium metavanadate, niobium oxalate, ammonium molybdate, telluric acid etc. The resulting solution is then dried typically in air at 100 to 150° C. and calcined in a flow of inert gas, such as, those selected from the group consisting of $N_2$, He, Ar, Ne and mixtures thereof at 200 to 600° C., preferably at 300 to 500° C. The calcining step may take from 1 to 20, typically, from 5 to 15 usually about 10 hours. The resulting oxide is a friable solid typically insoluble in water.

The Support

There are several ways the oxidative dehydrogenation catalyst may be supported.

In one embodiment, the support may have a low surface area, preferably, less than 50 $m^2/g$, more preferably, less than 20 $m^2/g$. The support may be prepared by compression molding. At higher pressures, the interstices within the ceramic precursor being compressed collapse. Depending on the pressure exerted on the support precursor, the surface area of the support may be from about 20 to 5 $m^2/g$, preferably 18 to 10 $m^2/g$.

There is a safety advantage using low surface area supports in that there is a reduced probability that an interstitial space may be filled only with oxidant providing a source of ignition.

The low surface area support could be of any conventional shape, such as, spheres, rings, saddles, etc. These types of supports would be used in more conventional reactors where a mixed stream or sequential stream of gaseous reactants pass over the supported catalyst and the ethane is converted to ethylene. There are a number of other approaches in the prior art where, for example, a mixed bed of supported catalyst and a reversible metal oxide may be passed together through a reaction zone to release oxide to the reaction and then regenerate the oxide. In some embodiments, the reversible metal oxide may contact a screen or permeable membrane having the supported catalyst on the other side together with a stream of ethane to release oxygen to the reaction.

In an alternate embodiment described below, the catalyst may be supported on a surface of a permeable membrane defining at least part of the flow path for one reactant and the other reactant flows over the opposite surface of the ceramic to permit the oxidant and ethane to react on the ceramic surface.

It is important that the support be dried prior to use. Generally, the support may be heated at a temperature of at least 200° C. for up to 24 hours, typically, at a temperature from 500° C. to 800° C. for about 2 to 20 hours, preferably 4 to 10 hours. The resulting support will be free of adsorbed water and should have a surface hydroxyl content from about 0.1 to 5 mmol/g of support, preferably, from 0.5 to 3 mmol/g of support.

The amount of the hydroxyl groups in silica may be determined according to the method disclosed by J. B. Peri and A. L. Hensley, Jr., in *J. Phys. Chem.*, 72 (8), 2926, 1968, the entire contents of which are incorporated herein by reference.

The dried support may then be compressed into the required shape by compression molding. Depending on the particle size of the support, it may be combined with an inert binder to hold the shape of the compressed part.

The support for the catalyst may be a ceramic or ceramic precursor formed from oxides, dioxides, nitrides, carbides and phosphates selected from the group consisting of silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

Preferred components for forming ceramic membranes include oxides of titanium, zirconium, aluminum, magnesium, silicon and mixtures thereof.

Loadings

Typically, the catalyst loading on the support provides from 0.1 to 20 weight % typically from 5 to 15 weight %, preferably from 8 to 12 weight % of said catalyst and from 99.9 to 80 weight %, typically, from 85 to 95 weight %, preferably, from 88 to 92 weight % of said support.

The catalyst may be added to the support in any number of ways. For example the catalyst could be deposited from an aqueous slurry onto one of the surfaces of the low surface area support by impregnation, wash-coating, brushing or spraying. The catalyst could also be co-precipitated from a slurry with the ceramic precursor (e.g., alumina) to form the low surface area supported catalyst.

The support and catalyst may be combined and then comminuted to produce a fine particulate material having a particle size ranging from 1 to 100 micron. The comminution process may be any conventional process including ball and bead mills, both rotary, stirred and vibratory, bar or tube mills, hammer mills, and grinding discs. A preferred method of comminution is a ball or bead mill.

The particulate catalyst may be used in an oxidative dehydrogenation reactor. The reactor may have a single or multiple beds, preferably, multiple beds.

Figure 11:
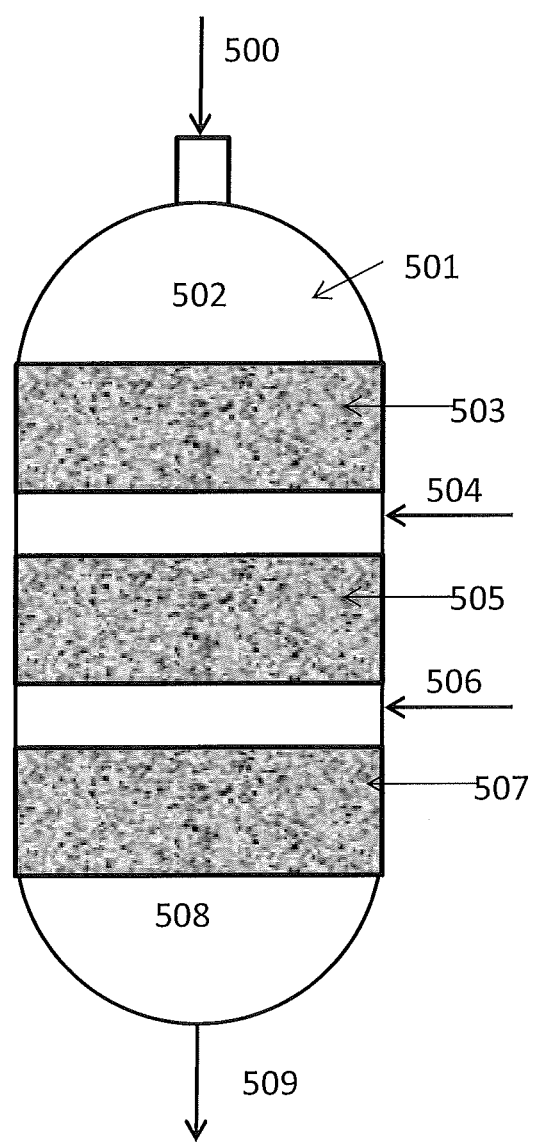
FIG. 11 is a schematic diagram of an oxidative dehydrogenation reactor having multiple beds.

FIG. 11 shows a schematic diagram of an oxidative dehydrogenation reactor containing three spaced apart fixed beds of catalyst.

In FIG. 11, the ethane or ethane containing gas 500 enters the reactor generally shown at 501 by an inlet 502. The ethane or ethane containing gas enters the first catalyst bed 503. Oxygen or an oxygen containing gas 504 flows into a space below the first catalyst bed 503 and a second catalyst bed 505. The oxygen flows into each bed. The stream of oxygen and partially reacted ethane or ethane containing gas flows into a second bed of catalyst 505. Further, oxygen or oxygen containing gas 506 flows into the second space between the second catalyst bed 505 and the third catalyst bed 507. The reactants continue to react in the third catalyst bed and the resultant stream of ethylene flows into collector (footer) 508 and out exit 509.

The Membrane

As noted above, the support should have a low surface area, preferably, less than 50 $m^2/g$, more preferably, less than 20 $m^2/g$. The support may be prepared by compression molding. At higher pressures, the interstices within the ceramic precursor being compressed collapse. Depending on the pressure exerted on the support precursor, the surface area of the support may be from about 20 to 10 $m^2/g$. The support will be porous and will have a pore volume from about 0.1 to 3.0 ml/g, typically, from 0.3 to 1.0 ml/g. The pore size of the ceramic may be small. Preferred pore size (diameter) ranges from about 3 to 10 nm. The small pore diameter is helpful in the ceramic membrane application as it helps maintain the pressure drop across the membrane so that a break in the membrane is readily detected by a sudden change in pressure. Additionally, the small pore diameter promotes a more uniform distribution of the reaction over the entire catalyzed surface of the membrane. That is, if larger pores are used, a majority of the oxygen tends to diffuse through the portion of the ceramic the oxygen containing gas initially comes in contact with. The remaining portion of the ceramic is largely unused.

The ceramic support may be prepared from the ceramic material using conventional techniques. For example, the starting material may be cleaned, washed and dried (or spray dried) or produced from a sol/gel of the ceramic and where necessary ground or milled to the appropriate particle size. The powder may be subjected to benefication, such as, acid or base washing to alter the pore size of the ceramic.

The resulting powder is dried or calcined to remove associated water as noted above (water of hydration, etc.) and may be formed into a suitable substrate, preferably, tubular, by, for example, compression molding or isostatic compaction at pressures from about 5 to 200 MPa (725 to 29,000 psi), with or without a binder and sintering at temperatures to fuse the particles. (e.g., at temperatures from about 0.5 to 0.75 of the melting temperature of the ceramic material.

Other techniques may be used, such as, tape casting or slip casting of slurries and the subsequent "punching of" the required shape, such as, circular, square or annular, etc. For example, annular sections could be "stacked" to produce a "tube".

While a tube is generally considered cylindrical, it could have any cross section shapes, such as, square, rectangular, hexagonal or stars, etc. It the case of a non-cylindrical tube, wall sections could be made by slip casting and then hermetically joining the wall sections together to form a central passage defined by an outer ceramic wall. The joints need to be hermetically sealed to prevent oxygen coming in contact with the ethane feed and forming an explosive mixture. Glass cement or a ceramic cement or slip would be used for this purpose. A hermetic seal also needs to be at the ends of the tube where it enters and exits the reactor or joins to the steel parts of the reactor.

In some embodiments, once the ceramic tube is prepared, the catalyst may be deposited on the surface of the tube in contact with the ethane.

The ceramic membrane may have a thickness from about 0.1 to 10 cm, typically, from 1 to 8 cm, preferably, from 2 to 7 cm.

While ceramics are strong they can be brittle. It is preferred to have a supporting structure at least on one side, preferably, the outside of the ceramic tube. Most preferably, there is a support structure on the outside and inside of the tube. The structure should be in the form of a mesh or a web having holes there through to permit the oxygen containing gas to pass through the support and the ceramic to react at the surface of the tube bearing the catalyst. The support may be any material suitable for use at the reactor operating temperatures. From a cost point of view, a steel mesh is likely most cost effective. Preferably, the steel is a stainless steel. The support structure should provide sufficient integrity to the tube to permit a shutdown of the reactor, if the ceramic is breached (e.g., becomes cracked, etc.)

One or more tubes are then placed inside the reactor. In one embodiment, the reactor is designed to have a plug flow of feedstock (e.g., primarily, ethane) through a passage between the reactor shell and the ceramic tube and a flow of oxygen containing gas through the ceramic tube. There are a number of arrangements that come to mind. The reactor could comprise several shorter tubes placed end to end to provide a tube of appropriate length. Or the design could be similar to a core shell heat exchanger with a number of parallel tubes through which the oxygen containing gas is passed with and an enclosed shell providing a passage between the external wall of the reactor and the ceramic tubes defining a flow path for the ethane. The flow paths might be reversed (ethane on the interior and oxygen on the exterior of the tube).

Figure 9:
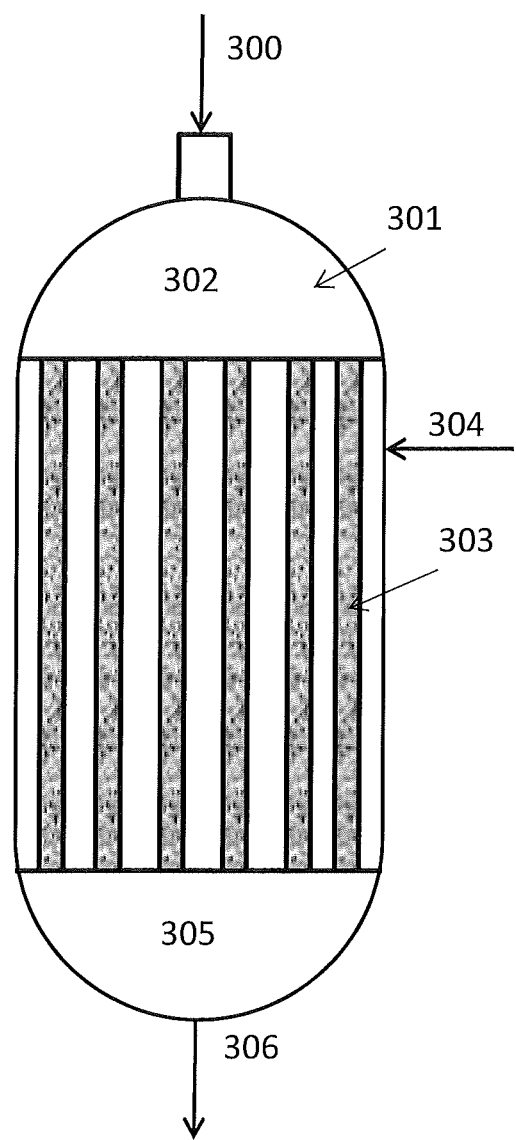
FIG. 9 is a schematic diagram of one embodiment of an oxidative dehydrogenation reactor with a bundle of membrane tubes.

FIG. 9 shows an embodiment of a membrane (ceramic tube) oxidative dehydrogenation reactor. The reactor is generally shown as 301. The reactor comprises an inlet 302 into which a stream of ethane or an ethane containing gas stream flows. The ethane passes through the ceramic membrane tubes 303 to a collector 305. Oxygen or an oxygen containing gas 304 is fed to the tube bundle so the oxygen is on the outside of the tubes. The ethane or ethane gas 300 reacts with the oxygen as it passes down the tube to form ethylene. The ethylene is collected in the collector (footer) 305 and exits the reactor at 306.

Figure 10:
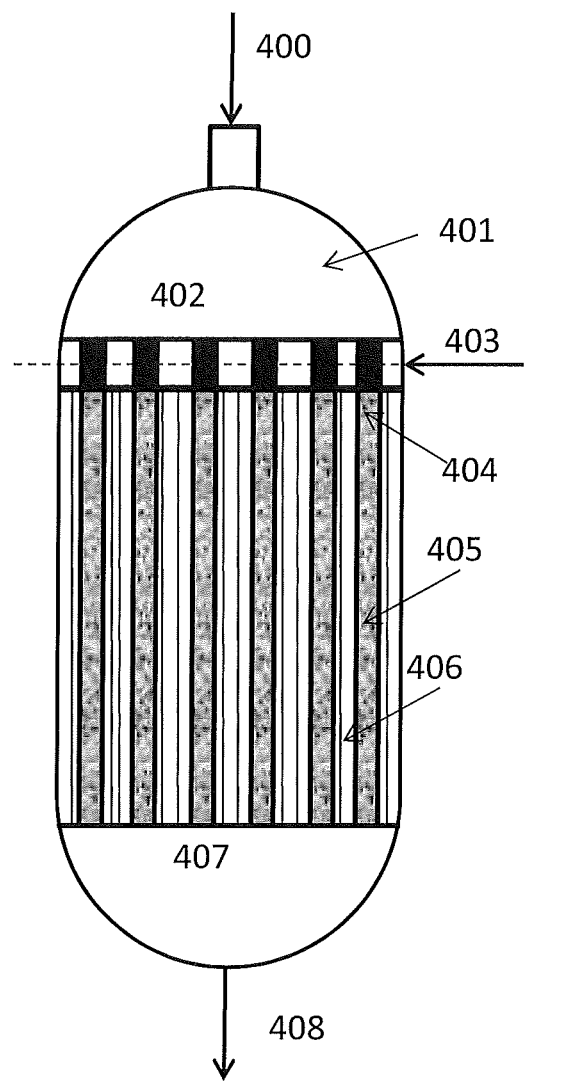
FIG. 10 is a schematic diagram of one embodiment of an oxidative dehydrogenation reactor with an oxygen header above the separated ceramic tubes.
Figure 10:
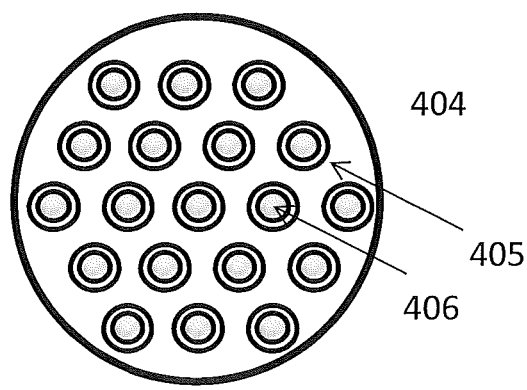

FIG. 10 shows a further embodiment in which the ethane or ethane gas 400 enters the reactor generally shown as 401 through an inlet or 402. The oxygen or oxygen containing gas 403 enters a tube and shell type plate shown as 404. There are a series of ceramic membrane tubes 406 encased in a steel shell 405. The ceramic membrane tubes 406 extend up to the header 402. As a result, the ethane or ethane containing gas 400 flows down the interior of the ceramic membrane tubes and the oxygen flows down the annular space between the exterior of the ceramic membrane tube 406 and the steel shell 405. The ethane is converted to ethylene and exits the ceramic membrane tubes into collector (footer) 407 and exits at 408. One advantage of this design is if a ceramic membrane loses integrity only excess oxygen enters that tube. This is easily detected by an oxygen detector (not shown) which may be at the exit of each tube 406 or in the collector 407. Then the reactor can be safely shut down and the damaged tube may be located.

The flows of the reactants may be concurrent or counter current (e.g., ethane up the outside of the tube and oxygen down the inside of the tube).

The feed to the reactor comprises two separate flows to opposite sides of a tube. In one embodiment, one flow, preferably, to the internal surface of the tube is an oxygen containing gas which is selected from the group consisting of oxygen, mixtures comprising from 100 to 21 vol. % of oxygen and from 0 to 79 vol. % of one or more inert gases. Some inert gases may be selected from the group consisting of nitrogen, helium and argon and mixtures thereof. Preferably, the oxygen containing gas is air as it provides for a much simpler plant operation.

The second flow, in some embodiments to the outside of the tube comprises one or more, $C_2$-$C_6$, preferably $C_2$-$C_4$ paraffins, most preferably, pure or undiluted ethane or an ethane containing gas. Most preferably, the ethane should have a purity greater than 90%, preferably, greater than 95%, most preferably, greater than 98%. However, it may be possible to operate with more dilute paraffin feeds, typically, comprising at least 60 wt. %, most preferably, not less than 80 wt. % of ethane and less than 40 wt. %, most preferably, less than 20 wt. % of one or more gases selected from the group consisting of methane, nitrogen, helium, argon and mixtures thereof. Preferably, the ethane containing gas is undiluted ethane as it provides for a much simpler plant operation and better productivity (space-time yield).

The ratios of the gas components will be a function of the method of operating the reaction to reach either the complete consumption of oxygen, or complete consumption of ethane, or both. The further separation will include separation of ethylene from unreacted ethane or admixed gases (methane, $CO_2$, inert gases, oxygen). The oxygen containing gas flow rate has to be large enough to provide sufficient oxygen to the catalyst to provide the oxygen needed for the oxidative dehydrogenation reaction. In one embodiment, in the ceramic membrane mode, the hydrocarbon stream passes over the oxidative dehydrogenation catalyst, optionally containing one or more metal oxides capable of releasing oxygen to the oxidative dehydrogenation catalyst. The feed rate of oxygen gas should be sufficient to keep the catalyst active but low enough to minimize carryover of oxygen into product olefin (ethylene). One can calculate the ratio of oxygen to paraffin based on the stoichiometry of the reaction. However, the reaction will also be affected by the take up and release rate of the oxygen to and from the catalyst, because oxygen is fed to the opposite side of the membrane and is supplied to the active mixed oxide catalyst through the porous ceramic membrane. The rate of oxygen supply is regulated by the pressure differential ($\Delta P$) from the oxygen side of the ceramic varying typically from 0.05 to 0.5 atm. Typically, the molar ratio of hydrocarbon (paraffin) to oxygen feed may range from 1:1 to 3:1, preferably, from 1.5:1 to 2.5:1. Given the foregoing, one of ordinary skill in the art will be able to determine the preferred ratio and flow rates of the two gas flows for the ceramic membrane mode. The shutdown of the oxygen flow results in fast but reversible loss of the ethane conversion.

The Reaction

The oxidative dehydrogenation may be conducted at temperatures from 300° C. to 550° C., typically, from 300° C. to 500° C., preferably, from 350° C. to 450° C., at pressures from 0.5 to 100 psi (3.447 to 689.47 kPa), preferably, from 15 to 50 psi (103.4 to 344.73 kPa), and the residence time of the paraffin in the reactor is typically from 0.002 to 30 seconds, preferably, from 1 to 10 seconds. The ethane feed should be of purity of preferably, 95%, most preferably, 98%. Preferably, the process has a selectivity for olefin (ethylene) of greater than 95%, preferably, greater than 98%. The gas hourly space velocity (GHSV) will be from 500 to 30000 $h^{-1}$, preferably greater than 1000 $h^{-1}$. The space-time yield of ethylene (productivity) in g/hour per Kg of the catalyst should be not less than 900, preferably, greater than 1500, most preferably, greater than 3000, most desirably, greater than 3500 at 350 to 400° C. It should be noted that the productivity of the catalyst will increase with increasing temperature until the selectivity is sacrificed.

The conversion of ethane to ethylene should be not less than 80%, preferably, greater than 90%, most preferably, 95% or greater.

Oxygen Scavenging

The amount of oxygen that is entrained in the product ethylene stream should be minimized for further processing. However, there will likely be some small amount of oxygen in the product stream. It is highly desirable that the oxygen be removed from the product stream prior to further processing of the product stream. Immediately downstream of the oxidative dehydrogenation reactor may be a low temperature reactor to consume residual oxygen without consuming more than about 3 wt % of the ethylene produced. This low temperature reactor, typically, uses a catalyst which is a mixture of $Mn_2O_3$ and $CuMn_2O_4$, said mixture having an empirical formula Cu—$Mn_xO_p$, wherein, x is from 0.1 to 8 and p is a number to satisfy the valence state of the mixed catalyst. The low temperature oxygen scavenging reactor operates at temperatures less than or equal to 400° C., typically from 100° C. to 400° C. The fuel for said low temperature reactor may be selected from the group consisting of methane, hydrogen, CO and mixtures thereof which may be either added to or present in the paraffin feed stream or added to the product stream from the oxidative dehydrogenation reactor in an amount sufficient to consume residual oxygen. In some embodiments, the oxygen scavenger, sometimes referred to as an afterburner, may be followed by a number of other process steps including a water wash, $CO_2$ removal, product separation which may include the typical $C_2$ splitter or other means to separate ethylene from ethane. One such embodiment is shown in FIG. 1.

In FIG. 1, feed streams of ethane or an ethane containing gas 1 and oxygen or an oxygen containing gas 2 are fed to an oxidative dehydrogenation reactor 3. The resulting stream of ethylene and co-products is fed to an oxygen scavenger (afterburner) 4. In the scavenger, there may be one or more catalysts to consume residual oxygen, preferably, at temperatures lower than that required for oxidative dehydrogenation. For example, the oxygen may react with hydrogen to produce water or with methane to produce CO or $CO_2$ without consumption of ethane. Preferably, in the oxygen scavenger, the residual oxygen in the product stream being treated is reduced to below 1000 ppm by volume. The resulting stream may then be treated with a liquid wash 5, such as, water containing scavenging agents, such as, sulphites, etc. The water soluble/reacted products leave the water wash as a stream of co-products 10. The resulting stream may then be subject to a $CO_2$ removal step 6 to produce a product, such as, ethylene oxide. Finally, the product goes to a product separation step 7 to separate ethylene 8 from residual ethane 9 which is recycled to stream 1.

Catalyst suitable for scavenging oxygen from ethylene or hydrocarbon streams are known as disclosed in U.S. Pat. No. 3,904,703 to Lo, assigned to El Paso and U.S. Published Application No. 2010/0256432 to Arnold assigned to Lummus noted above. More recent art on scavenging oxygen from hydrocarbons is disclosed in U.S. Pat. Nos. 6,747,066 and 6,992,112 issued Jun. 8, 2004 and Jan. 31, 2006, respectively, to Wang et al. assigned to ConocoPhillips Company.

The patents teach an oxygen scavenger of general formula

$$\alpha AO_x\text{-}\beta BO_y\text{-}\gamma CO_z$$

wherein: A is one of the precious metals Rh, Ru, Pd, Pt, Au, Ag, Os or Ir or is a transition metal chosen from the group consisting of Sc, Ti, V, Cr, Mn, Fe, Co, Ni, Cu, Zn, Nb, Mo, Tc, Hf, Ta, W, Re, preferably, Fe, Co, Ni, Mn, V or Mo or any combination of the above; B is a rare earth metal La, Ce, Pr, Nd, Pm, Sm, Eu, Gd, Th, Dy, Ho, Er, Tm, Yb, Lu, Sc, Y and Th, preferably, La, Yb, Sm or Ce; C is an element chosen from Group II (i.e., Be, Mg, Ca, Sr, Ba and Ra), Ill (i.e., B, Al, Ga, In, Tl) and IV (i.e., C, Si, Ge, Sn, Pb) elements of the Periodic Table of the Elements, preferably, Mg, Al or Si; O is oxygen; $\alpha$, $\beta$ and $\gamma$ are the relative molar ratios of each metal oxide and $\alpha$=0-0.2; $\beta$=0-0.5; $\gamma$=0.5-1; and x, y, z are the numbers determined by the valence requirements of the metals A, B, and C, respectively. Their value can be zero when the corresponding metal stays in the metallic states.

In a further option, the wash could contain pentafluoro decalin to extract the oxygen.

Preferably, at the exit of the oxidative dehydrogenation reactor is an oxygen sensor. The oxygen sensor is monitored to control the amount of additional feed needed to be added to the oxygen scavenger reactor, if any, to eliminate or substantially reduce the amount of residual oxygen in the product stream.

Additionally, there should be at least one thermocouple in the oxygen scavenging reactor. As noted above, the oxygen scavenging reaction is exothermic. Monitoring the oxygen content in the feed stream and the temperature of the oxygen scavenging reactor will give an indication of the integrity of the tube. A sudden rise in oxygen in the product stream and a sudden increase in the temperature of the oxygen scavenger reactor tends to indicate a breach of the ceramic membrane wall. If this occurs, the flow of oxygen to the reactor should be immediately terminated.

Separation of the Product Stream

The ethylene, preferably, after passing through the oxygen scavenger and a drier, may be fed to a C2 splitter downstream of the cracker to separate ethylene and ethane.

There are a number of options to combine a $C_2$ splitter and an oxidative dehydrogenation unit.

Figure 2:
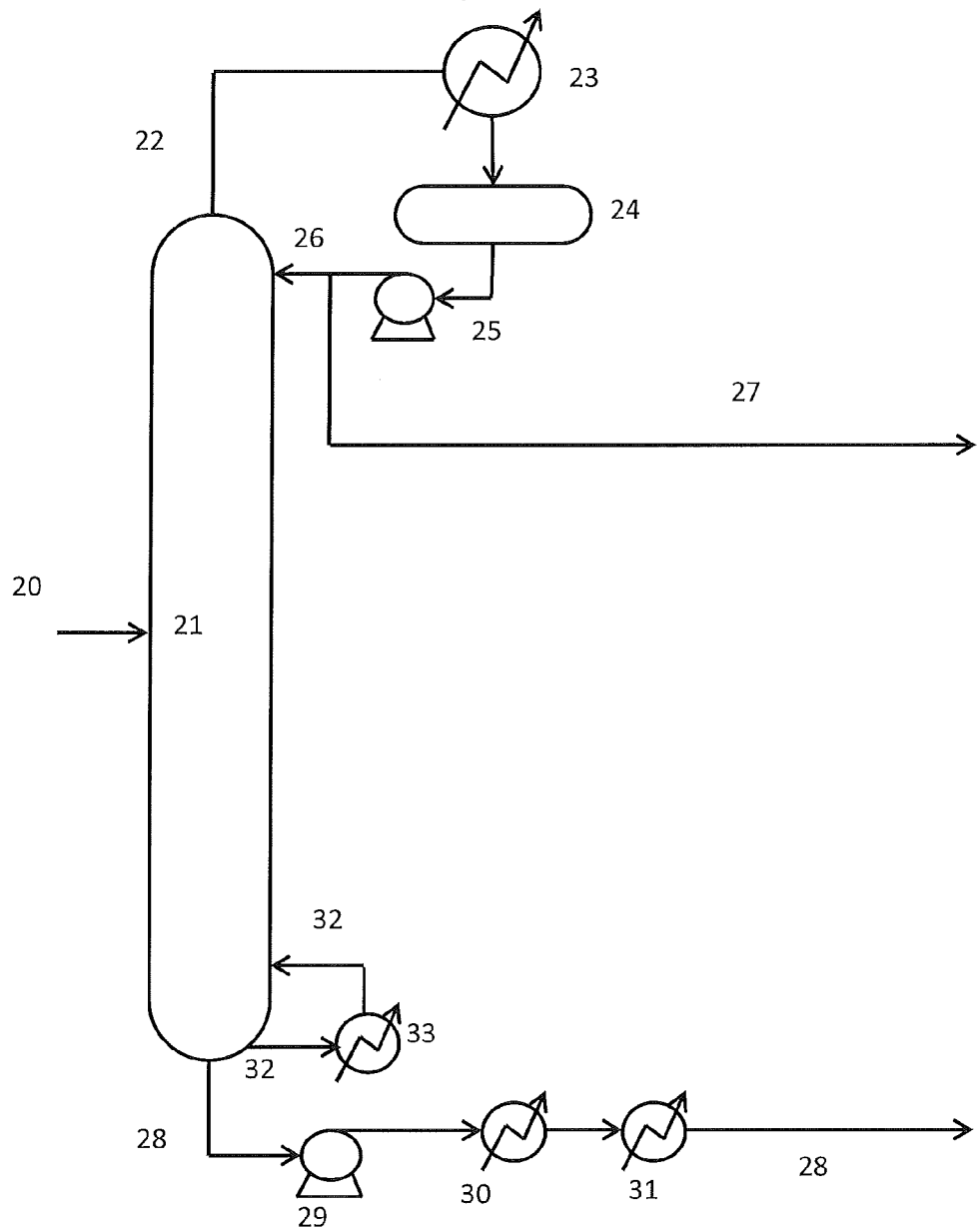
FIG. 2 is a schematic diagram of a conventional $C_2$ splitter (the base case).

FIG. 2 is a schematic diagram of a conventional $C_2$ splitter (cryogenic distillation tower). Feed 20, a mixture predominantly of ethylene and ethane, is fed to the column 21. An overhead stream of ethylene 22 leaves the top of the column 21 and passes through a condenser 23 to a reflux drum 24 and a pump 25. The condensed and re-pressurized stream is split into an ethylene product stream 27 and a high purity stream 26 fed back to the upper trays of the splitter 21. At the bottom of the splitter 21, a stream of ethane 28 passes through a pump 29 to two heaters 30 and 31 and is ready for further processing, such as, recycle to the cracker. Towards the bottom of the $C_2$ splitter 21, a stream of ethane 32 is taken and passed through a reboiler 33 and recycled back to the splitter 21. This is considered a base case against which the invention may be evaluated.

Figure 3:
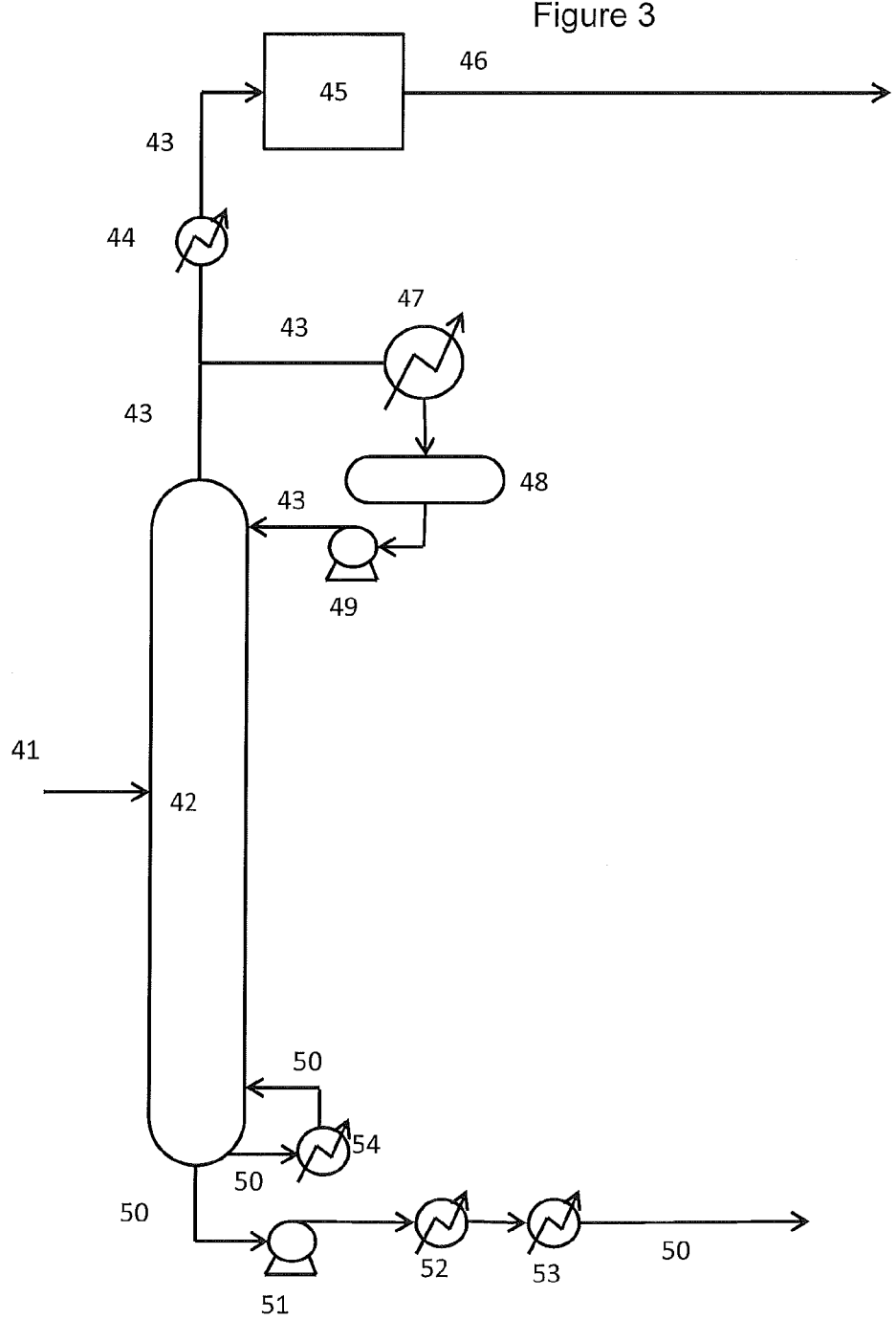
FIG. 3 is a schematic diagram of an oxidative dehydrogenation unit integrated with the overhead ethylene product stream of a $C_2$ splitter.

FIG. 3 is a schematic diagram of an embodiment of a $C_2$ splitter integrated with an oxidative dehydrogenation unit at the overhead stream (ethylene product stream). In this figure, a feed 41, predominantly of ethylene and ethane, is fed to splitter 42. A relatively pure stream of ethylene 43 exits the top of the $C_2$ splitter 42. A portion of the stream 43 is fed to a condenser 47, a reflux drum 48 and a pump 49 and fed back to the $C_2$ splitter 42. The remaining portion of product stream 43 is feed to a heater 44 and then to the oxidative dehydrogenation unit 45 resulting in a stream 46 of ethylene and traces of $CO_2$. At the bottom of splitter 42, near or at the last tray, a stream 50 of ethane and co-products is taken. A portion of the product is passed through a reboiler 54 and the vaporized stream 50 is recycled to the $C_2$ splitter 42. The other portion of the ethane product stream is fed to a pump 51 and then through heaters 52 and 53 and the ethane stream 50 is ready for further processing.

Figure 4:
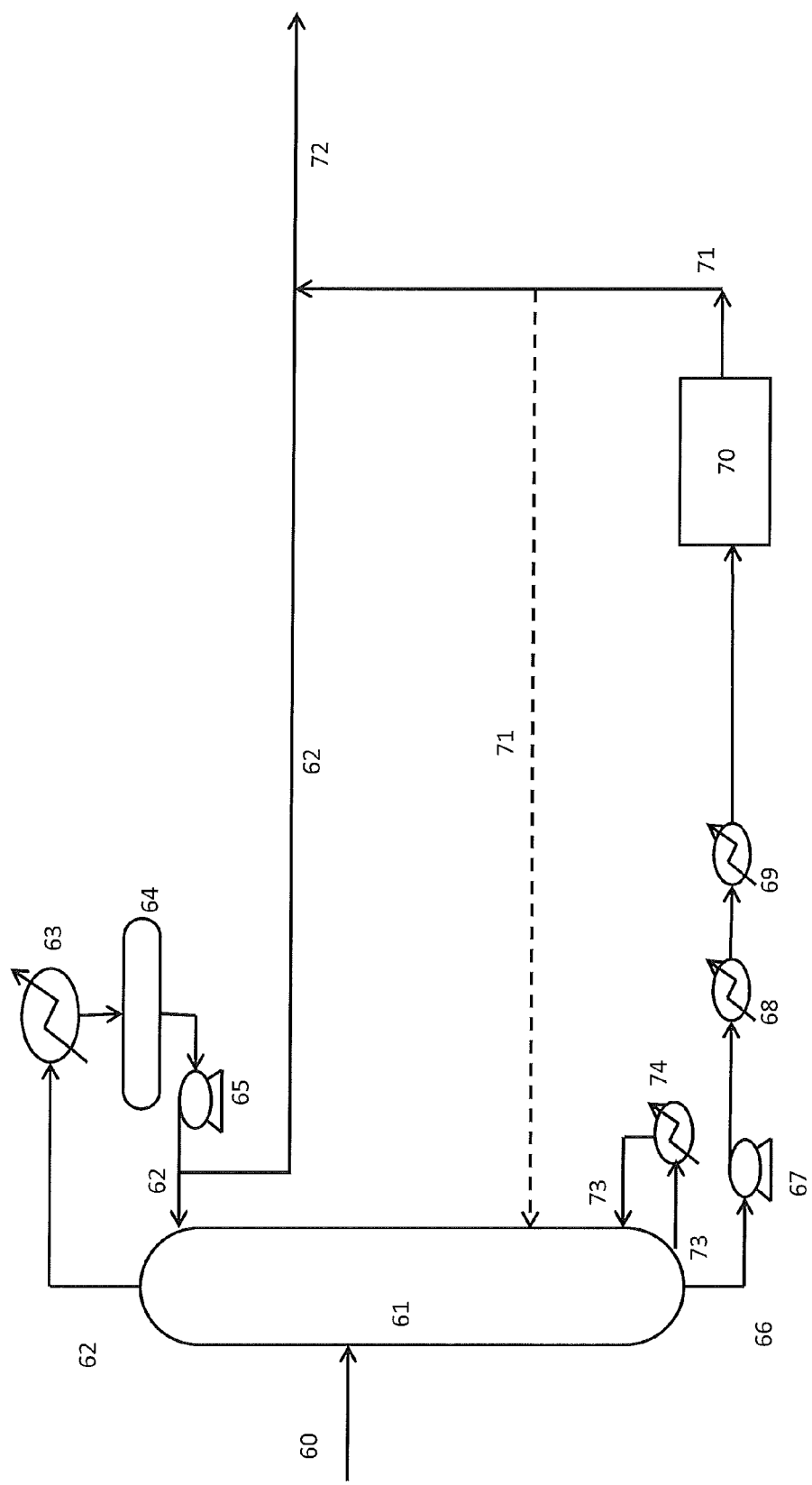
FIG. 4 is a schematic diagram of an oxidative dehydrogenation unit integrated with the bottom ethane recycle stream from a $C_2$ splitter.

FIG. 4 is an example of an embodiment of the invention of an oxidative dehydrogenation reactor integrated with the bottom product stream (ethane) from a $C_2$ splitter. In the figure, a feed of ethylene and ethane 60 is fed to the $C_2$ splitter 61. The overhead stream 62 largely ethylene is fed to a condenser 63, a reflux drum 64 and a pump 65. A portion of the product ethylene stream 62 is fed to the $C_2$ splitter 61 and a portion of the stream is available for further mixing with the product stream of oxidative dehydrogenation reactor 70 integrated with the bottom stream from the $C_2$ splitter 61. At the bottom of the $C_2$ splitter, a relatively pure stream of ethane 66 is fed to pump 67 and heaters 68 and 69. The stream is then fed to oxidative dehydrogenation unit 70 and the resulting stream of ethylene 71 is combined with overhead stream 62 to form product ethylene stream 72. Near the bottom of the $C_2$ splitter, above where stream 66 is taken off, a stream of ethane 73 is passed through a reboiler 74 and fed back to the splitter 61.

Figure 6:
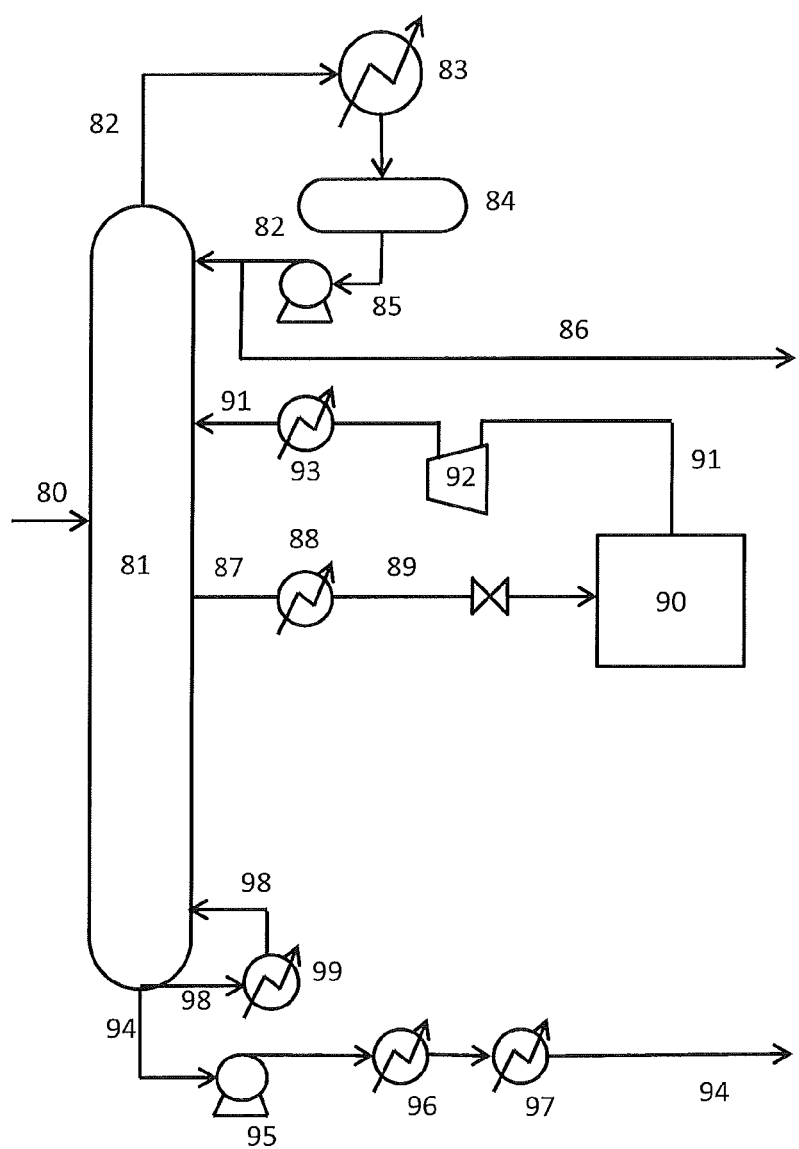
FIG. 6 is a schematic diagram of an oxidative dehydrogenation unit integrated internally with a C₂ splitter.

FIG. 6 is an embodiment of the invention showing integration of an oxidative dehydrogenation unit within the $C_2$ splitter. In FIG. 6, a stream of ethylene and ethane 80 is fed to $C_2$ splitter 81. The overhead stream of ethylene is fed to a condenser 83, reflux drum 84 and pump 85. A portion of stream 82 is fed back to the $C_2$ splitter. A portion of the ethylene stream 86 is available for downstream processing (e.g., polymerization to polyethylene, conversion to acetic acid, vinyl acetate). Towards the middle of the $C_2$ splitter a mixed stream of ethylene and ethane 87 is withdrawn. The stream passes through a heater 88, and, depending on the pressure of the stream, a pressure reduction device 89, for example, a turbo-expander. Stream 87 then passes through oxidative dehydrogenation unit 90. The product stream 91, having a higher ethylene content than stream 87, then passes through a compressor 92 and chiller 93 and is fed back to the $C_2$ splitter 81. At the bottom of the $C_2$ splitter 81, a relatively pure stream of ethane 94 is removed and fed to pump 95 and heaters 96 and 97. The resulting stream 94 is then ready for further processing (e.g., acetic acid) Stream 98 is fed to a reboiler 99 and returned to the splitter 81.

Figure 7:
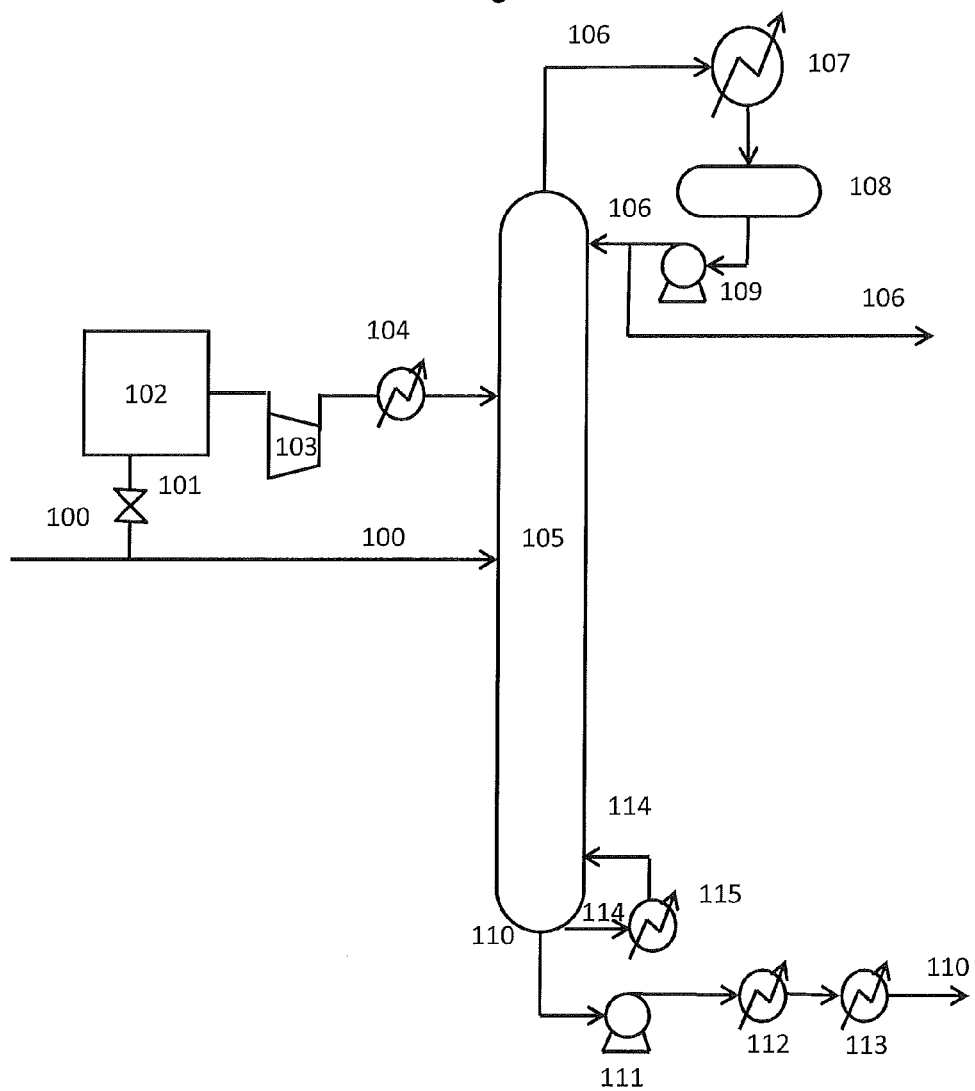
FIG. 7 is a schematic diagram of an oxidative dehydrogenation unit integrated with the feed upstream of a C₂ splitter.

FIG. 7 shows an embodiment of the invention where the oxidative dehydrogenation unit is integrated into the feed from the cracker to the $C_2$ splitter. In this embodiment, the ethylene and residual ethane product stream 100 from the cracker is split at valve 101. A portion of the feed 100 is fed to oxidative dehydrogenation unit 102. The resulting stream, which is higher in ethylene, is fed through a compressor 103 and then a condenser 104 and to the $C_2$ splitter 105. At the top of the $C_2$ splitter, an overhead stream of high purity ethylene 106 is fed to a condenser 107, reflux drum 108, pump 109 and back to $C_2$ splitter 105. A portion of the ethylene stream 106 is available for downstream processing. At the bottom of the $C_2$ splitter 105, a relatively pure stream of ethane 110 is removed and fed to pump 111 and heaters 112 and 113. The resulting stream 110 is then ready for further processing (e.g., acetic acid). Stream 114 is fed to a reboiler 115 and returned to the splitter 105.

Figure 8:
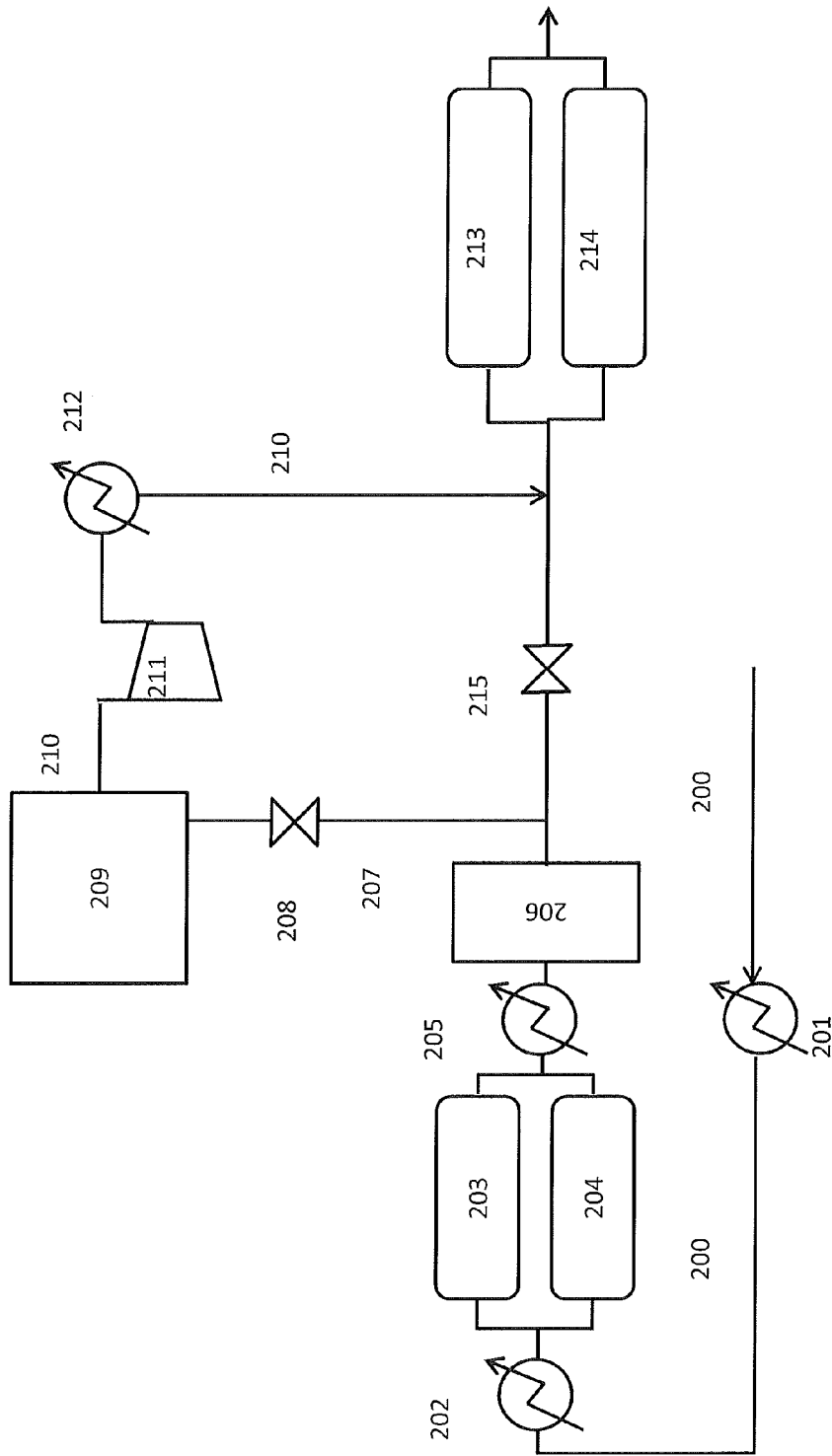
FIG. 8 is a schematic diagram of an oxidative dehydrogenation unit integrated upstream of the acetylene hydrogenation unit.

FIG. 8 is a schematic diagram of an embodiment of the invention in which an oxidative dehydrogenation unit is integrated downstream of the acetylene hydrogenation unit. In FIG. 8, a feed 200 predominantly comprising about 60 mole % ethylene and 40 mole % ethane from the cracker passes through a heaters 201 and 202. The feed 200 then passes to parallel hydrogenation units 203 and 204 to produce a stream 207 having an acetylene content less than about 1 ppm. The feed passes through chiller 205 to a green oil knock out drum 206. There are two lines from the knockout drum 206. One line goes through valve 215 to two driers. One line 207 passes through valve 208 to oxidative dehydrogenation unit 209. Stream 210 from the oxidative dehydrogenation unit 209 has a higher ethylene content than the stream from the hydrogenation units 203 and 204. Stream 210 passes through a compressor 211 and a cooler 212 and is mixed with the stream going to driers 213 and 214. By controlling valves 215 and 208, the amount of feed to the oxidative dehydrogenation unit 209 may be controlled from 0 to 100%.

Separation means other than, or used in parallel with, a $C_2$ splitter.

One method of separation of a product stream of ethylene and ethane is by absorption. The gaseous product stream comprising primarily ethane and ethylene may be contacted in a counter current flow with a heavier paraffinic oil, such as, mineral seal oil or medicinal white oil at a pressure up to 800 psi (about $5.5 \times 10^3$ kPa) and at temperatures from about 25° F. to 125° F. (about −4° C. to about 52° C.). The ethylene and lower boiling components are not absorbed into the oil. The ethane and higher boiling components are absorbed into the oil. The ethylene and lower boiling components may then be passed to the $C_2$ splitter. The absorption oil may be selectively extracted with a solvent, such as, furfural, dimethyl formamide, sulfur dioxide, aniline, nitrobenzene, and other known solvents to extract any heavier paraffins. This process is more fully described in U.S. Pat. No. 2,395,362 issued May 15, 1945 to Welling assigned to Phillips Petroleum Company, the contents of which are herein incorporated by reference.

Another separation method is an adsorption method. The adsorbent preferentially adsorbs one of the components in the product stream. The adsorption method typically comprises a train of two or more adsorption units so that when a unit has reached capacity the feed is directed to an alternate unit while the fully loaded unit is regenerated typically by one or more of a change in temperature or pressure or both.

There is a significant amount of art on the separation of ethylene and ethane using silver or copper ions in their +1 oxidation state. The olefins are preferentially absorbed into a complexing solution that contains the complexing agent selected from silver (I) or copper (I) salts dissolved in a solvent. Some silver absorbents include silver nitrate, silver fluoroborate, silver fluorosilicate, silver hydroxyfluoroborate, and silver trifluoroacetate. Some copper absorbents include cuprous nitrate; cuprous halides such as cuprous chloride; cuprous sulfate; cuprous sulfonate; cuprous carboxylates; cuprous salts of fluorocarboxylic acids, such as, cuprous trifluoroacetate and cuprous perfluoroacetate; cuprous fluorinated acetylacetonate; cuprous hexafluoroacetylacetonate; cuprous dodecylbenzenesulfonate; copper-aluminum halides, such as, cuprous aluminum tetrachloride; $CuAlCH_3Cl_3$; $CuAlC_2H_5Cl_3$; and cuprous aluminum cyanotrichloride. If the product stream has been dried prior to contact with the liquid absorbent, the absorbent should be stable to hydrolysis. The complexing agent preferably is stable and has high solubility in the solvent. After one absorbent solution is substantially loaded, the feed of product stream is switched to a further solution. The solution of absorbent which is fully loaded, is then regenerated through heat or pressure changes or both. This releases the ethylene.

These types of processes are described in U.S. Pat. No. 6,581,476 issued Feb. 11, 2003 to Culp et al. assigned to Union Carbide Chemicals & Plastics Corporation and U.S. Pat. No. 5,859,304 issued Jan. 12, 1999 to Barchas et al., assigned to Stone and Webster Engineering the contents of which are herein incorporated by reference.

As noted above, care needs to be taken in using these types of materials to avoid detonations.

In an alternative to the solution process, supports such as zeolite 4A, zeolite X, zeolite Y, alumina and silica, may be treated with a copper salt, to selectively remove carbon monoxide and/or olefins from a gaseous mixture containing saturated hydrocarbons (i.e., paraffins), such as, ethane and propane. U.S. Pat. No. 4,917,711 issued Apr. 17, 1990 to Xie et al., assigned to Peking University describes the use of such supported adsorbents, the contents of which are incorporated herein by reference.

Similarly, U.S. Pat. No. 6,867,166 issued Mar. 15, 2005 and U.S. Pat. No. 6,423,881 and Jul. 23, 2002 to Yang et al., assigned to the Regents of the University of Michigan, which are herein incorporated by reference, describe the use of copper salts and silver compounds supported, alternatively, on silica, alumina, MCM-41 zeolite, 4A zeolite, carbon molecular sieves, polymers such as Amberlyst-35 resin, and alumina to selectively adsorb olefins from gaseous mixtures containing olefins and paraffins. Both kinetic and thermodynamic separation behavior was observed and modeled. The adsorption of the olefin takes place at pressures from 1 to 35 atmospheres, preferably, less than 10 atmospheres, most preferably, less than 2 atmospheres at temperatures from 0 to 50° C., preferably from 25 to 50° C. and the desorption occurs at pressures from 0.01 to 5 atmospheres, preferably, 0.1 to 0.5 at temperatures from 70° C. to 200° C., preferably, from 100° C. to 120° C. In a further embodiment, the adsorbent may be a physical adsorbent selected from the group consisting of natural and synthetic zeolites without a silver or copper salt.

In general, the adsorbent may be alumina, silica, zeolites, carbon molecular sieves, etc. Typical adsorbents include alumina, silica gel, carbon molecular sieves, zeolites, such as, type A and type X zeolite, type Y zeolite, etc. The preferred adsorbents are type A zeolites, and the most preferred adsorbent is type 4A zeolite.

Type 4A zeolite, i.e., the sodium form of type A zeolite, has an apparent pore size of about 3.6 to 4 Angstrom units. This adsorbent provides enhanced selectivity and capacity in adsorbing ethylene from ethylene-ethane mixtures and propylene from propylene-propane mixtures at elevated temperatures. This adsorbent is most effective for use in the invention when it is substantially unmodified, i.e., when it has only sodium ions as its exchangeable cations. However, certain properties of the adsorbent, such as, thermal and light stability, may be improved by partly exchanging some of the sodium ions with other cations (other than silver or copper). Accordingly, it is within the scope of the preferred embodiment of the invention to use a type 4A zeolite in which some of the sodium ions attached to the adsorbent are replaced with other metal ions, provided that the percentage of ions exchanged is not so great that the adsorbent loses its type 4A character. Among the properties that define type 4A character are the ability of the adsorbent to selectively adsorb ethylene from ethylene-ethane mixtures and propylene from propylene-propane gas mixtures at elevated temperatures, and to accomplish this result without causing significant oligomerization or polymerization of the alkenes present in the mixtures. In general, it has been determined that up to about 25% (on an equivalent basis) of the sodium ions in 4A zeolite can be replaced by ion exchange with other cations without divesting the adsorbent of its type 4A character. Cations that may be ion exchanged with the 4A zeolite used in the alkene-alkane separation include, among others, potassium, calcium, magnesium, strontium, zinc, cobalt, manganese, cadmium, aluminum, cerium, etc. When exchanging other cations for sodium ions it is preferred that less than about 10 percent of the sodium ions (on an equivalent basis) be replaced with such other cations. The replacement of sodium ions may modify the properties of the adsorbent. For example, substituting some of the sodium ions with other cations may improve the stability of the adsorbent. As disclosed in U.S. Pat. No. 5,744,687 issued Apr. 28, 1998 to Ramachandran et al., assigned to the BOC Group, Inc., the contents of which are herein incorporated by reference.

A particularly preferred zeolite is ZSM-5.

In addition to zeolites, there are a number of titanium homologues referred to as ETS compounds.

U.S. Pat. No. 5,011,591 discloses the synthesis of a large pore diameter titanosilicate designated "ETS-10". In contrast to ETS-4 and CTS-1 (referenced below), the large pore titanosilicate material, ETS-10, which has pore diameters of about 8 A, cannot kinetically distinguish light olefins from paraffins of the same carbon number. Nevertheless, high degrees of selectivity have been reported for the separation of ethylene from ethane using as prepared ETS-10 zeolites; see: Al-Baghli and Loughlin in *J. Chem. Eng. Data* 2006, v51, p 248. The authors demonstrate that Na-ETS-10 is capable of selectively adsorbing ethylene from a mixture of ethylene and ethane under thermodynamic conditions, even at ambient temperature. Although, the reported selectivity for ethylene adsorption using Na-ETS-10 was high at ambient temperature, the adsorption isotherms for ethylene and ethane had highly rectangular shapes consistent with a low pressure swing capacity. Consequently, Na-ETS-10 is not readily applicable to pressure swing absorption processes (PSA), at least at lower or ambient temperatures.

However, cationic modification of as prepared Na-ETS-10 provides an adsorbent for the PSA separation of olefins and paraffins having the same number of carbon atoms, at ambient temperatures. The mono-, di- and tri-valent cations are selected from the group 2-4 metals, a proton, ammonium compounds and mixtures thereof. Some specific non-limiting examples of mono-, di, or tri-valent cations that can be used in the current invention include, $Li^+$, $K^+$, $Cs^+$, $Mg^{2+}$, $Ca^{2+}$, $Sr^{2+}$, $Ba^{2+}$, $Sc^{3+}$, $Y^{3+}$, $La^{3+}$, $Cu^+$, $Zn^{2+}$, $Cd^{2+}$, $Ag^+$, $Au^+$, $H^+$, $NH_4^+$, and $NR_4^+$ where R is an alkyl, aryl, alkylaryl, or arylalkyl group. The cationic modifiers are generally added to unmodified Na-ETS-10 in the form of a salt or an acid. The anionic counterion associated with the cationic modifier is not specifically defined, provided that it does not adversely affect the modification (i.e., cation exchange) reactions. Suitable anions include but are not limited to acetate, carboxylate, benzoate, bromate, chlorate, perchlorate, chorite, citrate, nitrate, nitrite, sulfates, and halide (F, Cl, Br, I) and mixtures thereof. Suitable acids include inorganic and organic acids, with inorganic acids being preferred. U.S. Pat. No. 8,017,825 issued Sep. 13, 2011 to Kuznicki et al, assigned to the Governors of the University of Alberta discloses the technology, the text of which is herein incorporated by reference.

As described in U.S. Pat. No. 6,517,611, heat treatment of ETS-4 gave a controlled pore volume zeolite material, dubbed "CTS-1" which is a highly selective absorbent for olefin/paraffin separations. The CTS-1 zeolite, which has pore diameters from about 3-4 A, selectively adsorbed ethylene from a mixture of ethylene and ethane through a size exclusion process. The pore diameter of CTS-1, allowed diffusion of ethylene, while blocking diffusion of ethane which was too large to enter the pores of the CTS-1 zeolite, thereby providing a kinetic separation. The CTS-1 adsorbent was successfully applied to a PSA process in which ethylene or propylene could be separated from ethane or propane, respectively.

The above adsorbents may be used in pressure swing adsorption units. Typically, the range of absolute pressures used during the adsorption step can be from about 10 kPa to about 2,000 kPa, (about 1.5 to about 290 pounds per square inch (psi)) preferably from about 50 kPa to about 1000 kPa (from about 7.2 to about 145 psi). The range of pressures used during the release of adsorbate (i.e., during the regeneration step) can be from about 0.01 kPa to about 150 kPa (about 0.0015 to about 22 psi), preferably, from about 0.1 kPa to about 50 kPa (about 0.015 to about 7.3 psi). In general, the adsorption step can be carried out at from ambient temperatures to above about 200° C., preferably less than 150° C., most preferably, less than 100° C., provided that the temperatures do not exceed temperatures at which chemical reaction of the olefin, such as, a oligomerization or polymerization takes place.

Another class of adsorbents is ionic liquids. Olefins and paraffins can be separated using ionic liquids of the formula a metal dithiolene selected from the group of complexes of the formulae:

$$M[S_2C_2(R^1R^2)]_2;\qquad\text{(i)}$$

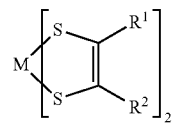

and $$M[S_2C_6(R^3R^4R^6R^7)]_2.\qquad\text{(ii)}$$

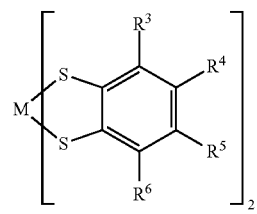

wherein M is selected from the group consisting of Fe, Co, Ni, Cu, Pd and Pt; and $R^1$, $R^2$, $R^3$, $R^4$, $R^5$, and $R^6$ are independently selected from the group consisting of a hydrogen atom, electron-withdrawing groups including those that are or contain heterocyclic, cyano, carboxylate, carboxylic ester, keto, nitro, and sulfonyl groups, hydrocarbyl radicals selected from the group consisting of $C_{1-4}$ alkyl groups, $C_{5-8}$, alkyl groups, $C_{2-8}$ alkenyl groups and $C_{6-8}$ aryl groups which hydrocarbyl radicals are unsubstituted or fully or partly substituted, preferably those substituted by halogen atoms. The ionic liquid may be used with a non-reactive solvent or co solvent. The solvent may be selected from the group of conventional aromatic solvents, typically toluene. Adsorption pressures may range from 200 psig to 300 psig ($1.3\times10^3$ to $2\times10^3$ kPag), preferably, below 250 psig ($1.7\times10^3$ kPag) and adsorption temperatures may range from ambient to 200° C., preferably, below 150° C., and the olefin may be released from the ionic liquid by one or more of lowering the pressure by at least 50 psig ($3.4\times10^2$ kPa) and increasing the temperature by not less than 15° C.

Downstream Unit Operations in the Complex

The complex may further comprise one or more unit operations using ethylene, ethane or both as a feed stream.

The further unit operations may be one or more of the following processes individually or in combination: a high pressure polyethylene plant; a gas phase polyethylene plant; a slurry phase polyethylene plant; a solution phase polyethylene plant; an acetic acid plant; a vinyl acetate plant; an ethylene glycol plant; an ethanol plant; an ethylene halide plant; an ethanol dehydrogenation plant; and an acetic acid dehydrogenation plant.

Ethylene Polymerization

The ethylene could be polymerized. There are a number of well-known methods for polymerizing ethylene.

The process could be a high pressure process. Typically, the pressures range from about 80 to 310 MPa (e.g., about 11,500 psi to about 45,000 psi) preferably from about 200 to 300 MPa (about 30,000 psi to about 43,500 psi) and the temperature ranges from 130° C. to 350° C., typically, from 150° C. to 340° C. The supercritical ethylene together with one or more of initiators, chain transfer agent and optional comonomers are fed to a high pressure reactor. A non-limiting example of a high pressure reactor is a tubular reactor. Tubular reactors may have a length from about 200 m to about 1500 m, and a diameter from about 20 mm to about 100 mm. The residence time is generally quite short, in the order of seconds to less than 5 minutes.

Solution and slurry polymerization processes are fairly well known in the art. These processes are conducted in the presence of an inert hydrocarbon solvent/diluent typically a $C_{4-12}$ hydrocarbon which may be unsubstituted or substituted by a $C_{1-4}$ alkyl group, such as, butane, pentane, hexane, heptane, octane, cyclohexane, methylcyclohexane or hydrogenated naphtha. An alternative solvent is Isopar E ($C_{8-12}$ aliphatic solvent, Exxon Chemical Co.).

The polymerization may be conducted at temperatures from about 20° C. to about 250° C. Depending on the product being made, this temperature may be relatively low, such as, from 20° C. to about 180° C., typically, from about 80° C. to 150° C., and the polymer is insoluble in the liquid hydrocarbon phase (diluent) (e.g., a slurry polymerization). The reaction temperature may be relatively higher from about 180° C. to 250° C., preferably, from about 180° C. to 230° C., and the polymer is soluble in the liquid hydrocarbon phase (solvent). The pressure of the reaction may be as high as about 15,000 psig for the older high pressure processes or may range from about 15 to 4,500 psig.

The polymerization could be gas phase, either fluidized bed or stirred bed. In the gas phase polymerization of a gaseous mixture comprising from 0 to 15 mole % of hydrogen, from 0 to 30 mole % of one or more $C_{3-8}$ alpha-olefins, from 15 to 100 mole % of ethylene, and from 0 to 75 mole % of an inert gas at a temperature from 50° C. to 120° C., preferably, from 75° C. to about 110° C., and at pressures, typically, not exceeding 3447 kPa (about 500 psi), preferably, not greater than 2414 kPa (about 350 psi).

Suitable olefin monomers include ethylene and $C_{3-10}$ alpha olefins which are unsubstituted or substituted by up to two $C_{1-6}$ alkyl radicals. Illustrative non-limiting examples of such alpha olefins are one or more of propylene, 1-butene, 1-pentene, 1-hexene, 1-heptene, 1-octene and 1-decene. The polymers prepared in accordance with the present invention have a wide range of molecular weight distribution (Mw/Mn or polydispersity). The molecular weight distribution may be controlled from about 2.5 to about 30.

The polyethylene polymers which may be prepared, typically, comprise not less than 60, preferably, not less than 70, most preferably, not less than 80 weight % of ethylene and the balance of one or more $C_{3-10}$ alpha olefins, preferably, selected from the group consisting of 1-butene, 1-hexene and 1-octene.

The catalyst used in the solution, slurry and gas phase polymerization may be one or more of chromium catalyst (Phillips type catalysts), Ziegler Natta type catalyst, and single site type catalysts including metallocene catalysts, constrained geometry catalysts, and bulky ligand heteroatom catalyst (e.g., phosphinimine catalysts), the catalyst are used with one or more activators, such as, aluminum halides, alkyl and oxalkyl compounds or MAO or borates.

In gas phase and slurry polymerizations, the catalyst and, typically, the activators are on a support such as alumina or silica.

Acetic Acid Unit

Ethylene or ethane or a mixture thereof may be oxidized to product acetic acid which may be reacted with further ethylene to produce ethyl acetate which may then be converted to vinyl acetate. Ethylene recovered in the separation processes noted above may be fed to an oxidation reactor together with oxygen and or water in a weight ratio from 1:0.1-250 by weight, such as 1:0.1-100 or 1:0-150 but preferably in a ratio 1:0.1-10 by weight in the presence of a supported catalyst. The oxidation reaction of this step of the present invention may suitably be carried out at a temperature in the range from 100 to 400° C., typically, in the range 140 to 350° C. at atmospheric or superatmospheric pressure, for example, in the range from 5 to 27 barg (50 to 270 kPa). There are a number of catalysts which may be used as in this type of reaction. Typically, the catalysts comprise molybdenum and tungsten with one or more transition metals having an atomic number from 44 to 47 and 77 to 79.

The resulting acetic acid may be fed to a further oxidation reactor together with ethylene to form ethyl acetate or with ethylene and an oxygen containing gas to form vinyl acetate.

There are a number of patents describing such processes including U.S. Pat. No. 7,211,688; EP-A 0407091; DE 19620542; WO 99/51339, the contents of which are herein incorporated by reference.

Acetic acid may also be dehydrogenated to produce ethylene. In this case, acetic acid from other sources, such as, fermentation, could be dehydrogenated to produce ethylene.

Ethylene Epoxide

Today ethylene oxide is mainly produced by a direct oxidation process in which ethylene is directly oxidized with air or purified oxygen (95% or greater) over a catalyst, typically, silver silicate, but on occasions elemental silver may be used, on a silica support (or co-precipitated with the silica support). The catalyst may contain activators or chemicals to reduce coking. The reaction occurs at temperature from 100° C. to 300° C., typically, from 140° C. to 250° C., preferably, less than 200° C. The pressure may be from about 7 psi (about 50 kPa) to about 300 psi (about $2.1 \times 10^3$ kPa). It is even more preferable to use a pressure from about 15 psi (about 104 kPa) to about 100 psi ($6.9 \times 10^2$ kPa). Typically, the space velocity may range from about 10 $hr^{-1}$ to about 15,000 $hr^{-1}$. Preferably, the space velocity is in the range from about 10 $hr^{-1}$ to about 6000 $hr^{-1}$. More preferably, the space velocity is in the range from about 50 $hr^{-1}$ to about 3000 $hr^{-1}$. U.S. Pat. No. 4,845,253 issued Jul. 4, 1989 to Bowman assigned to The Dow Chemicals Company discloses one such process, the contents of which are herein incorporated by reference.

Ethylene Glycol Unit

Ethylene epoxide is an intermediate for a number of downstream derivatives. Ethylene epoxide may be converted to ethylene glycol by reacting ethylene oxide with $CO_2$ in a presence of a catalyst, such as, alkali halides, quaternary ammonium halides, and quaternary phosphonium halides, to produce ethylene carbonate. The ethylene carbonate may be converted to ethylene glycol by reaction with water, typically, less than about 2:1 weight ratio of water to carbonate in the presence of a base ($Na_2CO_3$).

The process is more fully described in the Kirk Othmer Encyclopedia of Chemical Technology on-line edition.

Ethylene glycol may be converted into a number of other chemically useful compounds such as PET and PHET.

Ethanol Unit

The gas phase direct hydration of ethylene to ethanol may be conducted over a solid catalyst which is a porous substrate, typically, clay, silica or alumina impregnated with phosphoric acid. In this gas phase hydration process, it is typical to provide a mole ratio of about 0.4 to 0.8 mole of water per mole of ethylene. In some processes, phosphoric acid is added to the feed to make up for catalyst losses during the process. The reaction may be conducted at temperatures from about 235° to 250° C. and at pressures from about 700 psi to 1200 psi (($4.2 \times 10^3$ kPa to about $8.2 \times 10^3$ kPa).

Ethanol Dehydrogenation Unit

It will be recognized by those skilled in the art that in jurisdictions where there is a good supply of fermentable organic material (e.g., sugar cane) ethanol could be produced by fermentation and subsequently dehydrogenated over for example sulphuric acid to produce ethane.

Ethylene Halide Unit

The complex could contain a unit operation for the halogenation of ethylene to vinyl chloride or to ethylene chloride (EDC). EDC may be obtained by the direct halogenation or oxyhalogenation of ethylene, optionally, in the presence of oxygen. The direct halogenation may take place in the gas phase by reaction between ethylene and a gaseous halide (e.g., HCl) in the presence of a catalyst ($FeCl_3$). This is an exothermic reaction and heat needs to be removed from the reactor. In the oxyhalogenation process, oxygen and water are also present in the reactor and the catalyst component is CuCl.

The present invention will further be described by reference to the following examples. The following examples are merely illustrative of the invention and are not intended to be limiting. Unless otherwise indicated, all percentages are by weight and Portland cement is used unless otherwise specified.

EXAMPLES

The present invention will now be illustrated by the following non-limiting examples.

Example 1: Base Case $C_2$ Splitter (FIG. 2

Ethylene and ethane may be separated via cryogenic distillation; an example base case of ethylene and ethane separation via cryogenic distillation is shown in FIG. 2. In this example, the $C_2$ splitter feed is a 60% vapour fraction mixture comprised of 60 mole % ethylene and 40 mole % ethane at 1600 kPa. The feed stream enters the column on approximately tray 60, where trays are numbered from the top of the column down. The distillation column contains approximately 100 trays with 80% Murphree tray efficiency in the example shown. At the column pressure, the saturation temperature of pure ethylene is −37° C. and the saturation temperature of ethane is −16° C. The reflux ratio is 3.6, with a resulting ethylene distillation purity of 99.95 mole % and ethane bottoms purity of 99.5 mole %. The overhead condenser fully condenses the ethylene distillate and reflux, and requires a thermal duty of 35 MW. The kettle-type reboiler requires a thermal duty of 28 MW.

The example process conditions for the base case are summarized in Table 1.

TABLE 1

Example of $C_2$ splitter base case process conditions

| | $C_2$ Splitter Stream | | |
|---|---|---|---|
| | Feed | Bottoms | Distillate |
| Temperature (° C.) | −29 | −15 | −38 |
| Pressure (kPa) | 1617 | 1643 | 1559 |
| Vapor Frac | 0.6 | 0 | 0 |
| Mass Flow (kg/hr) | 129766 | 51445 | 78321 |
| Volume Flow (cum/sec) | 0.74 | 0.04 | 0.05 |
| Enthalpy (Gcal/hr) | −8 | −40 | 26 |
| Density (kg/cum) | 49 | 412 | 436 |

TABLE 1-continued

Example of $C_2$ splitter base case process conditions

| | $C_2$ Splitter Stream | | |
|---|---|---|---|
| | Feed | Bottoms | Distillate |
| Mass Flow (kg/hr) | | | |
| ETHYLENE | 78560 | 280 | 78279 |
| ETHANE | 51206 | 51164 | 42 |
| Mass Frac | | | |
| ETHYLENE | 0.605 | 0.005 | 0.999 |
| ETHANE | 0.395 | 0.995 | 536 PPM |
| Mole Flow (kmol/hr) | | | |
| ETHYLENE | 2800 | 10 | 2790 |
| ETHANE | 1703 | 1702 | 1 |

The base case is for an older $C_2$ splitter in operation at a NOVA Chemicals facility at Joffre, Alberta, Canada. When modeled using AspenTech Aspen Plus® software, the model-predicted production and heat/energy balance is not less than 95% of the actual operation of the plant.

In the following examples, the oxidative dehydrogenation unit was modeled on that of FIG. 9, a membrane reactor, using AspenTech Aspen Plus® software.

Example 2: Oxidative Dehydrogenation Integrated with the $C_2$ Splitter Overhead Stream (FIG. 3)

In this example, the oxidative dehydrogenation unit and $C_2$ splitter operation were modeled. The ethylene product purity was increased to at least 99.9 mole %, more preferably to 99.95 mole %.

By decreasing the ethylene purity of the overhead stream from 99.95 mole %, as shown in the base case example, to 95 mole % and decreasing the reflux rate accordingly, the ethylene distillate rate can be increased by approximately 6%. This process configuration is shown in FIG. 3. The overhead condenser duty for this example case is 25 MW and the reboiler duty is 27 MW, resulting in a 19% total thermal energy savings compared with the base case. The decrease in overhead condenser duty is due to the decrease in the reflux rate and because the condenser is condensing a smaller mass flow rate of ethylene product stream as compared to the base case. The auxiliary thermal and pumping duty required to condense and pressurize the ethylene product stream from the oxidative dehydrogenation unit from 100 kPa and 30 C to a saturated liquid at 1560 kPa is approximately 15 MW, therefore, the integrated process requires more energy than the base case. However, this process configuration allows for debottlenecking of the existing column by increasing the rate of ethylene production per unit feed and allows for an increase in column capacity by decreasing the reflux ratio and the required capacity of the overhead condenser. The results of the modeling are set forth in Table 2.

TABLE 2

Example of oxidative dehydrogenation integration with $C_2$ splitter overhead stream process conditions

| | $C_2$ Splitter Stream | | | | |
|---|---|---|---|---|---|
| | Feed | Bottoms | ODH Feed | Reflux | Overhead |
| Temperature (° C.) | −29 | −3 | −25 | −37 | −25 |
| Pressure (kPa) | 1617 | 1651 | 1568 | 1568 | 1568 |
| Vapor Frac | 0.6 | 0 | 1 | 0 | 1 |
| Mass Flow (kg/hr) | 129766 | 47042 | 82726 | 237500 | 320226 |
| Volume Flow (cum/sec) | 0.74 | 0.04 | 0.88 | 0.15 | 3.39 |
| Enthalpy (Gcal/hr) | −8 | −36 | 30 | 64 | 116 |
| Density (kg/cum) | 49 | 369 | 26 | 435 | 26 |
| Mass Flow (kg/hr) | | | | | |
| ETHYLENE | 78560 | 252 | 78309 | 224817 | 303126 |
| ETHANE | 51206 | 46789 | 4418 | 12683 | 17101 |
| Mass Frac | | | | | |
| ETHYLENE | 0.605 | 0.005 | 0.947 | 0.947 | 0.947 |
| ETHANE | 0.395 | 0.995 | 0.053 | 0.053 | 0.053 |
| Mole Flow (kmol/hr) | | | | | |
| ETHYLENE | 2800 | 9 | 2791 | 8014 | 10805 |
| ETHANE | 1703 | 1556 | 147 | 422 | 569 |

Example 3: Oxidative Dehydrogenation Unit Integrated with the Bottom Stream of the $C_2$ Splitter (FIG. 4)

In this example, oxidative dehydrogenation technology is modeled using AspenTech Aspen Plus® to debottleneck an existing $C_2$ splitter (base case configuration of the $C_2$ splitter is shown in FIG. 2). In this example, the oxidative dehydrogenation unit increases the ethylene purity to at least 99.9 mole %, more preferably to 99.95 mole %.

By decreasing the ethane purity of the bottoms stream from 99.5 mole %, as shown in the base case example, to 89.5 mole % and decreasing the reflux rate accordingly, the thermal duty required in the column can be reduced. An oxidative dehydrogenation unit could be applied to convert ethane in the bottoms stream to ethylene as shown in FIG. 4. The overhead condenser duty for this example case is 33 MW and the reboiler duty is 26 MW, resulting in a 6% total thermal energy savings compared with the base case. The decrease in overhead condenser duty is due to the decrease in the reflux rate and because the condenser is condensing a smaller mass flow rate of ethylene product stream as compared to the base case. The example conditions are summarized in Table 3. This process configuration allows for debottlenecking of the existing column by increasing the rate of ethylene production per unit feed and allows for an increase in column capacity by decreasing the reflux ratio and the required capacity of the overhead condenser and bottoms reboiler.

Figure 5:
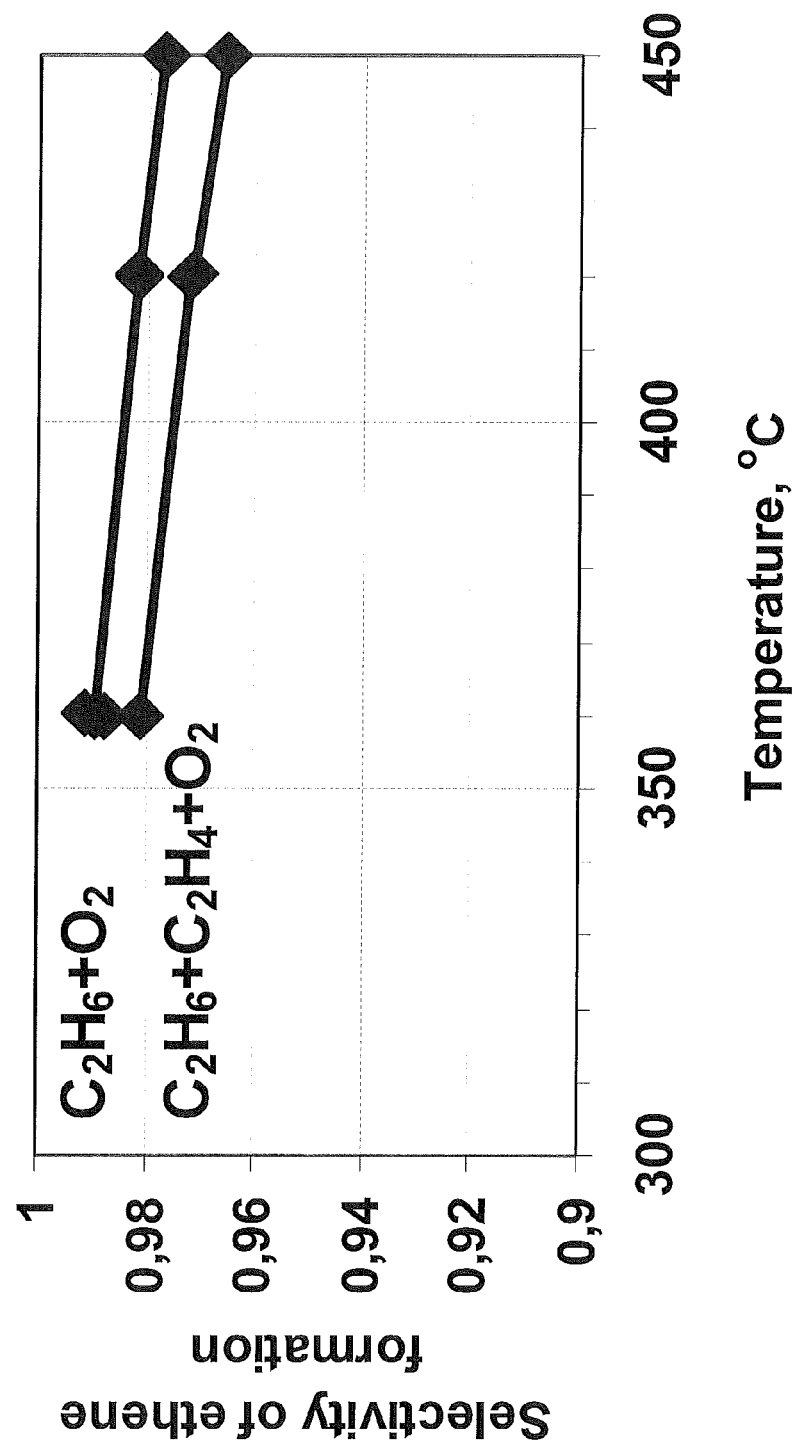
FIG. 5 is a graph showing the impact of temperature and ethylene content in the oxidative dehydrogenation reactor feed on selectivity toward ethylene with the outgoing mixture containing 61.9% C₂H₆₊₁₇.₆% C₂H₄₊₂₀.₅% O₂.

FIG. 5 illustrates that even 18 mole % of ethylene in the $C_2$ splitter bottom product does not significantly affect the selectivity of the oxidative dehydrogenation process.

The energy savings reported in the examples are from the separation area only, and it should also be considered that the ethane converted in an oxidative dehydrogenation unit in this example will not be recycled back to steam cracking furnaces, resulting in up to 40% energy savings in furnace operation as well as increasing the cracking furnaces throughput by up to 40% as a result of converting recycled ethane in an oxidative dehydrogenation unit and not recycling it back to the furnaces.

TABLE 3

Example of oxidative dehydrogenation integration with $C_2$ splitter bottoms stream process conditions

| | $C_2$ Splitter Stream | | |
|---|---|---|---|
| | Feed | Bottoms | Distillate |
| Temperature (° C.) | −29 | −18 | −38 |
| Pressure (kPa) | 1617 | 1643 | 1559 |
| Vapor Frac | 0.6 | 0 | 1 |
| Mass Flow (kg/hr) | 129766 | 56824 | 72941 |
| Volume Flow (cum/sec) | 0.74 | 0.04 | 0.05 |
| Enthalpy (Gcal/hr) | −8 | −38 | 24 |
| Density (kg/cum) | 49 | 415 | 436 |
| Mass Flow (kg/hr) | | | |
| ETHYLENE | 78508 | 5606 | 72902 |
| ETHANE | 51258 | 51218 | 39 |
| Mass Frac | | | |
| ETHYLENE | 0.605 | 0.099 | 0.999 |
| ETHANE | 0.395 | 0.901 | 537 ppm |
| Mole Flow (kmol/hr) | | | |
| ETHYLENE | 2798 | 200 | 2599 |
| ETHANE | 1705 | 1703 | 1 |

Example 4: Integration of an Oxidative Dehydrogenation Unit Between the Stages of the $C_2$ Splitter (FIG. 6)

The process of FIG. 6 was modeled using the AspenTech Aspen Plus® software to analyze the integrated system behaviour.

In this example, oxidative dehydrogenation technology is used to debottleneck the $C_2$ splitter whereby a sidedraw is taken from the $C_2$ splitter and the ethylene content of this slipstream is increased by at least 25%. This ethylene-enriched sidedraw is returned as a secondary feed stream to the $C_2$ splitter at a tray above the sidedraw tray.

In this example, approximately 20% of the feed molar flow rate is taken as a sidedraw from a tray with 20 mole % ethylene and 80 mole % ethane composition, and is converted in an oxidative dehydrogenation unit. The primary feed is composed of 60 mole % ethylene and 40 mole % ethane. With 50% conversion of ethane to ethylene and 0% conversion of ethylene to other products, the 60 mole % ethylene and 40 mole % ethane sidedraw is compressed and condensed to the column conditions existing on the same-composition tray. The process conditions simulated for this integration example are summarized in Table 4.

The reflux ratio required to achieve 99.95 mole % ethylene in the overhead product can be decreased by approximately 2%, however, due to the increased distillate rate in this example, the reflux rate must be increased by approximately 13% to maintain purity specifications. The boil-up rate required to minimize the ethylene content in the bottoms stream must be increased by approximately 17%. The ethylene distillate mass flow rate could be increased by approximately 15% in this example. The increase in ethylene produced per unit feed into the $C_2$ splitter would result in an increase in ethylene separation capacity in the $C_2$ splitter.

In this example, approximately 20% of the feed molar flow rate is taken as a slipstream and is hydrogenated in an oxidative dehydrogenation unit. The feed is composed of 60 mole % ethylene and 40 mole % ethane. With 50% conversion of ethane to ethylene and 0% conversion of ethylene to other products, the 80 mole % ethylene and 20 mole % ethane oxidative dehydrogenation product stream is compressed and condensed to the column conditions existing on the same-composition tray. The process conditions simulated for this integration example are summarized in Table 5.

The reflux ratio required to achieve 99.95 mole % ethylene in the overhead product can be decreased by approximately 10%, resulting in negligible increase in the reflux rate required. Also, negligible increase in the boil-up rate is required to minimize the ethylene content in the bottoms stream. The ethylene distillate mass flow rate could be increased by approximately 7% in this example. The increase in ethylene produced per unit feed into the $C_2$ splitter would result in an increase in ethylene separation capacity in the $C_2$ splitter.

TABLE 4

Example of oxidative dehydrogenation integration between the stages of the $C_2$ splitter process conditions

| | $C_2$ Splitter Stream | | | | |
|---|---|---|---|---|---|
| | Feed | Bottoms | Distillate | Sidedraw | ODH Product |
| Temperature (° C.) | −29 | −15 | −38 | −21 | −29 |
| Pressure (kPa) | 1617 | 1643 | 1559 | 1631 | 1665 |
| Vapor Frac | 0.6 | 0 | 0 | 0 | 0 |
| Mass Flow (kg/hr) | 129766 | 38909 | 90024 | 29660 | 28827 |
| Volume Flow (cum/sec) | 0.74 | 0.03 | 0.06 | 0.02 | 0.02 |
| Enthalpy (Gcal/hr) | −8 | −30 | 30 | −17 | −3 |
| Density (kg/cum) | 49 | 412 | 436 | 419 | 425 |
| Mass Flow (kg/hr) | | | | | |
| ETHYLENE | 78560 | 182 | 89975 | 5699 | 17296 |
| ETHANE | 51206 | 38727 | 48 | 23961 | 11531 |
| Mass Frac | | | | | |
| ETHYLENE | 0.605 | 0.005 | 0.999 | 0.192 | 0.6 |
| ETHANE | 0.395 | 0.995 | 536 PPM | 0.808 | 0.4 |
| Mole Flow (kmol/hr) | | | | | |
| ETHYLENE | 2800 | 6 | 3207 | 203 | 617 |
| ETHANE | 1703 | 1288 | 2 | 797 | 383 |

Example 6: Integration of an Oxidative Dehydrogenation Unit with the Feed to a $C_2$ Splitter (FIG. 7)

In this example, the process of FIG. 7 was modeled using AspenTech Aspen Plus®.

A slipstream is taken from the primary feed to the $C_2$ splitter and the ethylene content of this slipstream is increased by at least 25%. This ethylene-enriched slipstream is returned as a secondary feed stream to the $C_2$ splitter at a tray above the primary feed tray.

TABLE 5

Example of oxidative dehydrogenation integration with the feed stream of the $C_2$ splitter process conditions

| | C2S Stream | | | |
|---|---|---|---|---|
| | Feed | Bottoms | Distillate | ODH Product |
| Temperature (° C.) | −29 | −15 | −38 | −32 |
| Pressure (kPa) | 1617 | 1643 | 1559 | 1687 |
| Vapor Frac | 0.6 | 0 | 0 | 0 |
| Mass Flow (kg/hr) | 103813 | 46302 | 83121 | 25610 |
| Volume Flow (cum/sec) | 0.59 | 0.03 | 0.05 | 0.02 |

TABLE 5-continued

Example of oxidative dehydrogenation integration with the feed stream of the C₂ splitter process conditions

|  | C2S Stream | | | |
|---|---|---|---|---|
|  | Feed | Bottoms | Distillate | ODH Product |
| Enthalpy (Gcal/hr) | −6 | −36 | 27 | 3 |
| Density (kg/cum) | 49 | 412 | 436 | 426 |
| Mass Flow (kg/hr) | | | | |
| ETHYLENE | 62848 | 259 | 83076 | 20488 |
| ETHANE | 40965 | 46043 | 45 | 5122 |
| Mass Frac | | | | |
| ETHYLENE | 0.605 | 0.006 | 0.999 | 0.8 |
| ETHANE | 0.395 | 0.994 | 536 PPM | 0.2 |
| Mole Flow (kmol/hr) | | | | |
| ETHYLENE | 2240 | 9 | 2961 | 730 |
| ETHANE | 1362 | 1531 | 1 | 170 |

Example 7: Integration of an Oxidative Dehydrogenation Unit Base with the Acetylene Removal Unit Upstream from Driers (FIG. 8)

In this example, the feed stream to an oxidative dehydrogenation unit is the product from an acetylene hydrogenation reactor in a steam cracking plant. In this case, the ethane, which is present in the feed, is dehydrogenated at a conversion of at least 60% more preferably 80%, more preferably 99.5%.

Example 8: Integration of an Oxidative Dehydrogenation Unit with an Oil Refinery (No Figure)

In this example, the feed stream to an oxidative dehydrogenation unit is an ethane/ethylene mixed stream from an oil refinery, which may contain but is not limited to the mixed $C_2$ fraction from FCC, hydrocracking and hydrotreating operations. The ethylene content in this mixture can be from 8 volume % to 80 volume % In this case the ethane, which is present in the feed, is dehydrogenated at a conversion of at least 60% more preferably 80%, more preferably 99.5%.

Example 9: Integration of an Oxidative Dehydrogenation Unit with an Oil Sands/Bitumen Upgrader (No Figure)

In this example, the feed stream to an oxidative dehydrogenation unit is an ethane/ethylene mixed stream from an oil sands/bitumen upgrader, which may contain but is not limited to the mixed $C_2$ fraction from fluid coking, delayed coking and hydrocracking operations. The ethylene content in this mixture can be from 8 volume % to 80 volume %.

In this case the ethane, which is present in the feed, is dehydrogenated at a conversion of at least 60% more preferably 80%, more preferably 99.5%.

Example 10: Operation of a Membrane Oxidative Dehydrogenation Reactor with Bundled Membrane Tubes (FIG. 9)

In the present example, the membrane reactor consists of a bundle of membrane tubes, wherein the catalyst is loaded inside the tubes as shown in FIG. 9. This reactor design reduces the potential of membrane tube damage due to the different thermal expansion coefficients between the reactor vessel wall, catalyst and the membrane material. The internal reactor wall may be coated with ceramic to withstand the high temperature during any potential runaway reaction.

Three feed conditions are possible:
1. Ethane is preheated, oxygen is not preheated.
2. Oxygen is preheated, ethane is not preheated.
3. Both ethane and oxygen are preheated.

Example 11: Operation of a Membrane Oxidative Dehydrogenation Reactor with Enclosed Bundled Membrane Tubes (FIG. 10)

The reactor design considered in the present example is the same as Example 10, except that oxygen is supplied to the membranes through individual and separate tubes; each membrane has its own oxygen tube. This option could reduce the potential for multiple membrane tube damage if one tube is ruptured. The reactor has to be designed in a way that if one membrane is broken and no reaction is occurring, the oxygen level is safely diluted by the reaction products from the other membrane tubes. Also, an analyzer downstream of the reactor could detect an increase in the product oxygen content and shut down the reactor immediately for inspection of potential membrane damage.

Figure 12:
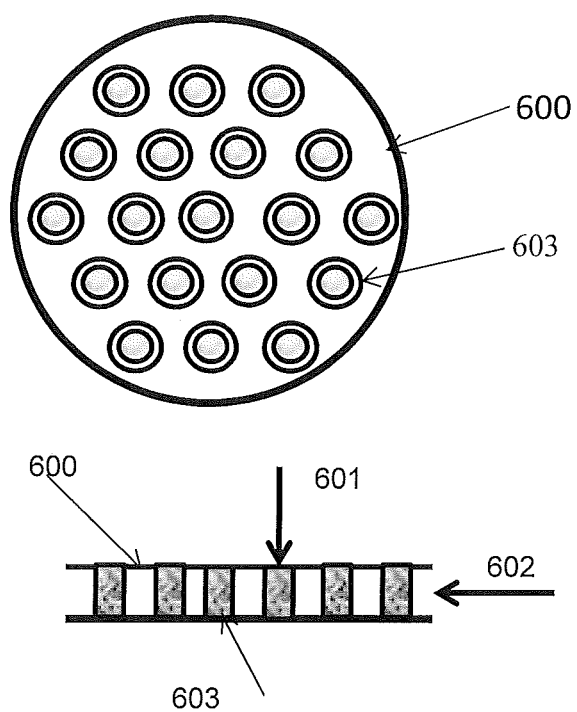
FIG. 12 show a mixing header for a feed to an oxidative dehydrogenation reactor.

Example 12: Operation of a Multiple Bed Oxidative Dehydrogenation Reactor (FIGS. 11 and 12)

In the multiple bed reactor approach shown in FIG. 11, oxygen and ethane are supplied to the first bed as either a pre-mixed fluid or the oxygen and ethane are mixed in the reactor inlet. The reactor can operate in either upward flow or downward flow modes of operation. The concentration of oxygen in the mixture supplied to each catalyst bed is such that the mixture is above its upper explosion limit (UEL). The maximum allowable amount of oxygen may be calculated based on the maximum allowable temperature in the reactor in the case of a runaway reaction. Oxygen is supplied at a temperature below the weight-averaged bed temperature (WABT) and acts as a quench gas.

Oxygen and hydrocarbons can be mixed together without ignition according to prior art outlined in US20100191005A1. The gas stream 601 can be filtered to reduce the presence of particles, which can be potential ignition sources. Oxygen 602 and hydrocarbons can also be mixed via the method shown in FIG. 12, where oxygen is supplied inside of a membrane or distributor screen. This screen can be coated with an oxidative dehydrogenation catalyst on the hydrocarbon site, whereby, the membrane is impermeable to gas on the upper surface 600. Oxygen can permeate the membrane and mix with hydrocarbons on the membrane surface 603.

Example 13: Ethane Oxidative Dehydrogenation on a Lab Scale in Two Catalyst Beds Operation In the present example, two lab-scale catalyst beds in series have been used to demonstrate oxidative dehydrogenation of ethane. Both catalyst beds are 0.2 $cm^3$ in volume. The first catalyst bed is charged with 281 mg of catalyst and the inlet gas volume flow rate is 900 $cm^3$/hr and is composed of 77.3 mol % ethane and 22.3 mol % oxygen. The second catalyst bed is charged with 290 mg of catalyst; the inlet gas for the second catalyst bed consists of the whole product from the first catalyst bed and 300 $cm^3$/hr of oxygen. The second catalyst bed inlet and outlet component mass flow rates are summarized in Table 6.

TABLE 6

Example ethane oxidative dehydrogenation on a lab scale in two
catalyst bed operation, second catalyst bed results

| Total inlet gas flow (g/hr) (58.3% C$_2$H$_6$ + 41.7% O$_2$) | | | Reaction temperature | Outlet gas flow (g/hr) | | | | | |
|---|---|---|---|---|---|---|---|---|---|
| Ethane | Oxygen | Sum | (° C.) | H$_2$O | Ethane | Ethylene | Oxygen | CO* | CO$_2$ |
| 0.874 | 0.668 | 1.542 | 383 | 0.161 | 0.627 | 0.225 | 0.507 | 0.004 | 0.021 |
| 0.874 | 0.668 | 1.542 | 401 | 0.251 | 0.500 | 0.350 | 0.415 | 0.003* | 0.037 |
| 0.874 | 0.668 | 1.542 | 419 | 0.342 | 0.362 | 0.465 | 0.321 | 0.006 | 0.060 |
| 0.874 | 0.668 | 1.542 | 438 | 0.400 | 0.270 | 0.530 | 0.261 | 0.006* | 0.088 |

The present invention has been described with reference to specific details of particular embodiments thereof. It is not intended that such details be regarded as limitations upon the scope of the invention except insofar as and to the extent that they are included in the accompanying claims.

What is claimed is:

1. A chemical complex comprising one or more unit operations selected from the group consisting of a high pressure polyethylene unit, a gas phase polyethylene unit, a slurry phase polyethylene unit, a solution phase polyethylene unit, an acetic acid unit, a vinyl acetate unit, an ethylene epoxide unit, an ethylene glycol unit, an ethanol unit, an ethylene halide unit, an ethanol dehydrogenation unit, and an acetic acid dehydrogenation unit;

and a steam cracker feeding at least one of a C$_2$ cryogenic distillation tower and a hydrogenation unit to remove acetylene, the improvement consisting of integrating an oxidative dehydrogenation unit for the oxidative dehydrogenation of ethane in a mixed stream of ethylene and ethane;

wherein the product stream from the cracker is heated and fed to parallel hydrogenation units to produce a stream having less than 1 ppm acetylene, and passed through a knock out drum and split so that at least a portion of the resulting stream passes through an oxidative dehydrogenation unit to increase the ethylene content thereof, and returned to the product stream having less than 1 ppm of acetylene and the combined stream is dried for further processing;

wherein the oxidative dehydrogenation of ethane to ethylene is conducted at a temperature from 250° C. to 600° C., a pressure from 0.5 to 100 psi (3.4 to 689.5 kPa) and has a productivity of not less than 1000 g of olefin per kg of catalyst per hour in the presence of a catalyst selected from the group consisting of:

i) catalysts of the formula $$Ni_xA_aB_bD_dO_e$$

wherein
x is a number from 0.1 to 0.9, preferably from 0.3 to 0.9, most preferably from 0.5 to 0.85, most preferably 0.6 to 0.8;
a is a number from 0.04 to 0.9;
b is a number from 0 to 0.5;
d is a number from 0 to 0.5;
e is a number to satisfy the valence state of the catalyst;
A is selected from the group consisting Ti, Ta, V, Nb, Hf, W, Y, Zn, Zr, Si and Al or mixtures thereof;
B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof;
D is selected from the group consisting of Ca, K, Mg, Li, Na, Sr, Ba, Cs, and Rb and mixtures thereof; and
O is oxygen;

ii) catalysts of the formula $$Mo_fX_gY_hO_i$$

wherein
X is selected from the group consisting of Ba, Ca, Cr, Mn, Nb, Ta, Ti, Te, V, W and mixtures thereof;
Y is selected from the group consisting of Bi, Ce, Co, Cu, Fe, K, Mg, V, Ni, P, Pb, Sb, Si, Sn, Ti, U, and mixtures thereof;
f=1;
g is 0 to 2;
h=0 to 2, with the proviso that the total value of h for Co, Ni, Fe and mixtures thereof is less than 0.5;
i is a number to satisfy the valence state of the catalyst;

iii) catalysts of the formula $$V_xMo_yNb_zTe_mMe_nO_p$$

wherein Me is a metal selected from the group consisting of Ta, Ti, W, Hf, Zr, Sb and mixtures thereof; and
x is from 0.1 to 3;
y is from 0.5 to 1.5;
z is from 0.001 to 3;
m is from 0.001 to 5;
n is from 0 to 2
and p is a number to satisfy the valence state of the mixed oxide catalyst;

iv) catalysts of the formula $$Mo_aV_bNb_cTe_eO_n$$

wherein a=1.0; b=0.05 to 1.0, c=0.001 to 1.0, e=0.001 to 0.5, and n is determined by the oxidation states of the other elements; and v) catalysts of the formula $$Mo_aV_bX_cY_dZ_eM_fO_n$$

wherein X is at least one of Nb and Ta; Y is at least one of Sb and Ni; Z is at least of one of the Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); b=0.05 to 1.0; c=0.001 to 1.0; d=0.001 to 1.0; e=0.001 to 0.5; and f=0.001 to 0.3; and n is determined by the oxidation states of the other elements.

2. The chemical complex according to claim 1, wherein in said catalysts of the formula(iii) n is 0.

3. The chemical complex according to claim 1, wherein the oxidative dehydrogenation unit has a selectivity of not less than 95% to produce ethylene.

4. The chemical complex according to claim 3, wherein the oxidative dehydrogenation catalyst is supported on an inert porous ceramic membrane selected from oxides of titanium, zirconia, aluminum, magnesium, yttria, lantana, silica and their mixed compositions, to provide from 0.1 to 20 weight % of said catalyst and from 99.9 to 80 weight % of said inert porous ceramic membrane.

5. The chemical complex according to claim 4, wherein the oxidative dehydrogenation unit comprises an outer shell and one or more internal ceramic tubes defining a separate, flow passage for oxygen-containing gas on the interior of said tubes and a passage between the external wall of the reactor and the ceramic tubes defining a flow path for an ethylene-containing gas.

6. The chemical complex according to claim 5, wherein the ceramic tube further comprises an internal steel mesh and an external steel mesh.

7. The chemical complex according to claim 6, wherein the oxidative dehydrogenation of ethane to ethylene is conducted at a temperature from 300° C. to 550° C.

8. The chemical complex according to claim 6, wherein the ethylene halide unit is present and reacts ethylene, optionally in the presence of oxygen with a halide to produced one or more products selected from the group consisting of ethyl chloride, ethylene chloride, ethylene dichloride, ethyl bromide, ethylene bromide and ethylene dibromide.

9. The chemical complex according to claim 6, wherein the acetic acid unit is present and oxidizes one or more of ethane and ethylene from the oxidative dehydrogenation unit, the steam cracker or both to produce acetic acid.

10. The chemical complex according to claim 9, wherein acetic acid from the acetic acid unit is reacted with ethylene to produce vinyl acetate.

11. The chemical complex according to claim 3, wherein the oxidative dehydrogenation catalyst is supported on an inert ceramic support having a surface area from 20 to 5 $m^2/g$ selected from oxides of titanium, zirconia, aluminum, magnesium, yttria, lantana, silica and their mixed compositions, to provide from 0.1 to 20 weight % of said catalyst and from 99.9 to 80 weight % of said inert ceramic support.

12. The chemical complex according to claim 11, wherein the ethylene halide unit is present and reacts ethylene, optionally in the presence of oxygen with a halide to produced one or more products selected from the group consisting of ethyl chloride, ethylene chloride, ethylene dichloride, ethyl bromide, ethylene bromide and ethylene dibromide.

13. The chemical complex according to claim 11, wherein the acetic acid unit is present and oxidizes one or more of ethane and ethylene from the oxidative dehydrogenation process, the steam cracker or both to produce acetic acid.

14. The chemical complex according to claim 13, wherein acetic acid from the acetic acid unit is reacted with ethylene to produce vinyl acetate.

* * * * *